US007807156B1

(12) United States Patent
Croft et al.

(10) Patent No.: US 7,807,156 B1
(45) Date of Patent: Oct. 5, 2010

(54) METHODS OF TREATING OX40 MEDIATED RECALL IMMUNE RESPONSES

(75) Inventors: Michael Croft, San Diego, CA (US); Shahram Salek-Ardakani, San Diego, CA (US)

(73) Assignee: La Jolla Institute for Allergy and Immunology, La Jolla, CA (US)

( * ) Notice: Subject to any disclaimer, the term of this patent is extended or adjusted under 35 U.S.C. 154(b) by 162 days.

(21) Appl. No.: 11/873,149

(22) Filed: Oct. 16, 2007

Related U.S. Application Data

(63) Continuation of application No. 10/661,358, filed on Sep. 11, 2003, now Pat. No. 7,291,331.

(60) Provisional application No. 60/410,534, filed on Sep. 11, 2002.

(51) Int. Cl.
*A61K 39/395* (2006.01)
(52) U.S. Cl. .................................................. 424/130.1
(58) Field of Classification Search ....................... None
See application file for complete search history.

(56) References Cited

U.S. PATENT DOCUMENTS

| 5,457,035 | A | 10/1995 | Baum et al. ................. 435/69.5 |
| 5,759,546 | A | 6/1998 | Weinberg et al. ......... 424/179.1 |
| 5,783,665 | A | 7/1998 | Baum et al. .................. 530/350 |
| 6,312,700 | B1 | 11/2001 | Weinberg ................. 424/278.1 |
| 6,566,082 | B1 | 5/2003 | Weinberg et al. .......... 435/7.24 |
| 2002/0054873 | A1 | 5/2002 | Weinberg ................ 424/141.1 |
| 2004/0009174 | A1 | 1/2004 | Arndt et al. .............. 424/146.1 |
| 2004/0136992 | A1* | 7/2004 | Burton et al. ............ 424/145.1 |

FOREIGN PATENT DOCUMENTS

| WO | WO 95/21251 | 8/1995 |
| WO | WO 99/42585 | 8/1999 |

OTHER PUBLICATIONS

Arestides RS, et al. Costimulatory molecule OX4OL is critical for both Th1 and Th2 responses in allergic inflammation. Eur J Immunol. 2002; 32:2874-80.
Hoshino A, et al. Critical role for OX 40 ligand in the development of pathogenic Th2 cells in a murine model of asthma. Eur J Immunol. 2003; 33:861-9.
Amha Gebre-Hiwot Jember, et al., Development of Allergic Inflammation in a Murine Model of Asthma Is Dependent on the Costimulatory Receptor OX40, J. Exp. Med. 193(3):387-392 (2001).
Huang, Z., et al., Structural Chemistry and Therapeutic Intervention of Protein-Protein Interactions in Immune Response, Human Immunodeficiency Virus Entry, and Apoptosis, Pharmacology and Therapeutics, 2000, 86:201-215.
Imura, Akihiro, et al., The Human OX40/gp34 System Directly Mediates Adhesion of Activated T Cells to Vascular Endothelial Cells, J. Exp. Med., 1996, 183:2185-2195.
Imura, Akihiro, et al., OX40 Expressed on Fresh Leukemic Cels from Adult T-Cell Leukemia Patiens Mediates Cell Adhesion to Vascular Endothelial Cells: Implication fo rhte Possible Involvements of OX40 in Leukemic Cell Infiltration, Blood, 1997, 89:2951-2958.
Basic Facts about Asthma, 2003, at cdc.gov/asthma/faqs.
Evans, Dean E., et al., Engagement of OX40 enhances antigen-specific CD4+ T cell mobilization/memory development and humoral immunity: Comparison of αOX-40 with αCTLA-4, *J. of Immunology*, 2001, 167:6804-6811.
Gramaglia, Irene, et al., Ox-40 Ligand: A potent costimulatory molecule for sustaining primary CD4 T cell responses, *J. of Immunology*, 1998, 161:6510-6517.
Gramaglia, Irene, et al., The OX40 costimulatory receptor determines the development of CD4 memory by regulating primary clonal expansion, *J. of Immunology*, 2000, 165:3043-3050.
Henderson, William R., et al., Soluble IL-4 Receptor Inhibits Airway Inflammation Following Allergen Challenge in a Mouse Model of Asthma, *J. of Immunology*, 2000, 164:1086-1095.
Kjaergaard, Jorgen, et al., Augmentation versus inhibition: Effects of conjunctional OX-40 receptor monoclonal antibody and IL-2 treatment on adoptive immunotherapy of advanced tumor, *J. of Immunology*, 2001, 167: 6669-6677.
Kobayashi, Tetsuto, et al., An Essential Role of Mast Cells in the Development of Airway Hyperresponsiveness in a Murine Asthma Model, *J. of Immunology*, 2000, 164:3855-3861.
Maxwell, Joseph R., et al., Danger and OX40 receptor signaling synergize to enhance memory T Cell survival by inhibiting peripheral deletion, *J. of Immunology*, 2000, 164:107-112.

(Continued)

*Primary Examiner*—Ilia Ouspenski
(74) *Attorney, Agent, or Firm*—Pillsbury Winthrop Shaw Pittman LLP

(57) ABSTRACT

T cell memory can persist in the absence of antigen. However, some memory cells by default are subject to signals accompanying periodic antigen exposure. OX40 is essential to the extent and persistence of Th2 memory when antigen is re-encountered. In an animal model of allergic asthma, inhibiting OX40/OX40L signaling during the secondary response to inhaled antigen suppressed lung inflammation. Inhibiting OX40 at the time of memory cell reactivation reduced the longevity of memory with further inflammation prevented upon tertiary encounter with antigen.

24 Claims, 8 Drawing Sheets

OTHER PUBLICATIONS

Mellis, CM, Is asthma prevention possible with dietary manipulation?, *Med. J. Aust.*, 2002, 177:S78-S80.

Owens et al., The genetic engineering of monoclonal antibodies, *Journal of Immunological Methods*, 1994, 168: 149-165.

Pan, Ping-Ying, OX40 Ligation enhances primary and memory cytoxic T lymphocyte responses in an immunotherapy for hepatic colon metastases, *Molecular Therapy*, 6(4):528-536 (2002).

Roitt, Ivan M.; Brostoff, Jonathan; and Male, David K., *Immunology*, 2nd ed., 1989, pp. 1.1, 2.8, 8.1-8.2, Gower Medical Publishing, 34-42 Cleveland Streeet, London W1P 5Fb, England.

Salek-Ardakani, Shahram, et al., OX40 (CD134) Controls Memory T Helper 2 Cells that Drive Lung Inflammation, *J. Exp. Med.*, 2003, 198(2):315-324.

Weatherill, Amy R., et al., OX40 Ligation enhances cell cycle turnover of Ag-activated CD4 T Cell in Vivo, *Cellular Immunology*, 209, 63-75 (2001).

Weinberg, Andrew D., et al., Blocking OX-40/OX-40 Ligand interaction in vitro and in vivo leads to decreased T cell function and amelioration of experimental allergic encephalomyelitis, *J. of Immunology*, 1999, 162: 1818-1826.

Weinberg, Andrew D., Ox40: Targeted imunotherapy-implications for tempering autoimmunity and enhancing vaccines, *TRENDS in Immunology*, 20(2):102-109 (Feb. 2002).

Yoshioka, T., et al., Contribution of OX40/OX40 Ligand interaction to the pathogenesis of rheumatoid arthritis, *Eur. J. Immunol.* 30:2815-2823 (2000).

\* cited by examiner

US 7,807,156 B1

METHODS OF TREATING OX40 MEDIATED RECALL IMMUNE RESPONSES

RELATED APPLICATIONS

This application is a continuation application of U.S. application Ser. No. 10/661,358, filed Sep. 11, 2003, now U.S. Pat. No. 7,291,331 which claims priority to application Ser. No. 60/410,534, filed Sep. 11, 2002.

GOVERNMENT SUPPORT

This work was made with government support under grant AI050498 awarded by the National Institutes of Health. The government has certain rights in the invention.

FIELD OF THE INVENTION

The invention relates generally to immune responses and agents useful for modulating immune response. More particularly, the invention relates to recall immune responses, and methods of reducing and preventing symptoms, such as inflammation, associated with a recall response.

BACKGROUND

The factors that regulate T cell memory are of great interest, and of potential significance to understanding how to augment immunity and how to suppress adverse immune reactions. Data gathered many years ago promoted the idea that the longevity of effective memory was dependent on periodic exposure to antigen (Gray, D., Matzinger, P. (1991) J Exp Med. 174:969). In contrast, more recent data have challenged this idea and suggested that individual memory T cells can survive for extended periods in the absence of specific antigen, and in some cases in the absence of any apparent signals (Lau et al., Nature (1994) 369:648; Tanchot et al., Science (1997) 276:2057; and Swain et al., Science (1999) 286:381).

Rather than one theory being incorrect, there are scenarios that may incorporate both ideas. For example, an alternative hypothesis is that a memory T cell can persist and be functional in the absence of signals accompanying antigen recognition, but that when antigen is encountered again, the individual memory T cell is now subject to both positive and negative signals that will dictate its further persistence and/or further functionality. It can be envisioned that some types of memory, such as that driving allergic asthma, are maintained in the face of antigen insults. Although it can be argued that other types of memory may not involve periodic exposure to antigen, at some stage those memory T cells will be required to respond to their specific antigen and hence again be susceptible to any positive and negative signals that accompany that recognition event. In either case, it is therefore essential to define the nature of those positive and negative signals.

Apart from the TCR/peptide/MHC interaction, the most likely sources of positive and negative signals are membrane bound molecules of the Ig and TNFR superfamilies. Although there is abundant data on the requirement of members of these families in effective priming of naïve T cells and hence dictating the development of memory T cells, there is virtually no data on whether they can influence reactivity or persistence of a memory T cell once it has been generated. For example, although it is widely accepted that the response of a naïve T cell is positively controlled by signals from cell surface costimulatory receptors, the role of costimulation in regulating a memory T cell has not been established. Based on experiments in vitro a number of years ago, it was postulated that memory T cells are less dependent, or independent, of costimulation for activation (Croft et al., J Immunol. (1994) 152:2675; Byrne et al., J Immunol. (1988) 141:3249; and Luqman, M., Bottomly, K. J Immunol. (1992) 149:2300). Negative data from in vivo studies trying to block CD28 costimulation from B7 also supported this idea (Lu et al., J Immunol. (1995) 54:1078; Gause et al., Exp Parasitol. (1996) 84:264; and Harris et al., Eur J Immunol. (1999) 29:311), while only a few publications have suggested that a secondary response may be susceptible to CD28 signals (Keane-Myers et al., J Immunol. (1997) 158:2042; and Tsuyuki et al., J Exp Med. (1997) 185:1671).

In contrast to costimulation through CD28, it is now clear that a number of additional receptors exist that may be crucial to a long-lived T cell response. The contribution of these other pathways to maintenance and functionality of antigen-specific memory T cells is unknown. OX40 (CD134) is one such costimulatory member, belonging to the TNFR superfamily. OX40 (CD134) has been shown to mediate potent costimulatory activity upon binding to its cognate ligand, OX40L, expressed on APC (Weinberg et al., Semin Immunol. (1998) 10:471). OX40 is not constitutively expressed on naïve T cells but is induced 24-48 hr after recognition of antigen (Mallett et al., EMBO J. (1990) 9:1063; Calderhead et al., J Immunol. (1993) 151:5261; Baum et al., EMBO J. (1994) 13:3992; and Gramaglia et al., J Immunol. (1998) 161:6510. OX40L, a member of the TNF family, is also inducible being expressed on activated B cells, dendritic cells, and macrophage-like cells (Baum et al. (1994), supra; Gramaglia et al. (1998), supra; Al-Shamkhani et al., J Biol Chem. (1997) 272:5275; Stuber et al., Immunity (1995) 2:507; Ohshima et al., J Immunol. (1997) 159:3838; and Weinberg et al., J Immunol. (1999) 162:1818).

Previous work has demonstrated that OX40 and OX40L control the development of a number of primary T cell responses (Gramaglia et al. (1998), supra, Gramaglia et al., J Immunol. (2000) 165:3043, Rogers et al., Immunity (2001) 15:445, Weinberg et al., (1999), supra, Kopf et al., Immunity (1999) 11:699, Chen et al., Immunity (1999) 11:689, Murata et al., J Exp Med. (2000) 191:365, Jember et al., J Exp Med. (2001) 193:387, Akiba et al., J Exp Med. (2000) 191:375, Tsukada et al., Blood (2000) 95:2434, Higgins et al., J Immunol. (1999) 162:486, Yoshioka et al., Eur J Immunol. (2000) 30:2815, Nohara et al., J Immunol. (2001) 166:2108). OX40 appears to function by suppressing T cell death by maintaining high levels of anti-apoptotic proteins such as Bcl-xL and Bcl-2 (Rogers et al., Immunity (2001) 15:445) and inhibiting expression or activity of pro-apoptotic proteins such as Bad and Bim. This conclusion is supported by in vivo studies where agonist antibodies directed to OX40 on a responding naïve CD4 cell enhanced primary T cell expansion and survival, promoting the development of greater numbers of memory T cells (Gramaglia et al., (2000), supra; Maxwell et al., J. Immunol. (2000) 164:107). However, no studies have addressed whether these interactions are required by memory T cells.

OX40 is down-regulated after the effector phase of primary T cell responses and returns to baseline levels within a week after initial antigen encounter. Significantly, antigen-primed $CD4^+$ T cells can upregulate OX40 more rapidly than naïve T cells and the majority can re-express OX40 within four hours of antigen stimulation (Gramaglia et al. (1998), supra). Similarly, an anergic T cell, which also represents an antigen-experienced cell, albeit functionally hyporesponsive, can also re-express OX40 at low levels and be receptive to OX40 engagement resulting in enhanced functionality (Bansal-Pakala et al., Nat Med. (2001) 7:907).

Previous studies concluded that memory T cells largely had a reduced requirement for costimulatory signals and, therefore, may not be susceptible to interventions that target such membrane bound molecules as OX40 (Croft, M. Curr Opin Immunol. (1994) 6:431). For example, blocking B7-CD28 interactions during secondary responses to the nematode parasites *Heligmosomoides polygyrus* and *Nippostrongylus brasiliensis*, or immunogenic anti-mouse IgD antibody treatment, failed to inhibit memory Th2 responses, whereas blocking CD28 at the time of priming was suppressive (Lu et al., J Immunol. (1995) 54:1078, Gause et al., *Exp Parasitol*. (1996) 84:264, Harris et al., Eur J Immunol. (1999) 29:311). These and other observations therefore imply that activation of memory Th2 cells may be costimulation, or at least B7/CD28, independent.

SUMMARY

Methods of reducing or inhibiting a recall immune response are provided. In one embodiment, a method includes administering an amount of an agent that reduces or inhibits OX40 or OX40L signaling, expression or activity sufficient to reduce or inhibit a recall immune response. In one aspect, the immune response is mediated at least in part by OX40 or OX40 ligand (OX40L). Recall responses include any secondary, tertiary or subsequent immune response to an antigen that occurs in any organ or tissue (e.g., lung, spleen, lymph node or vessel, or skin).

Methods of alleviating, ameliorating, reducing and inhibiting one or more symptoms associated with a secondary or subsequent immune response to an antigen, including responses mediated at least in part by OX40 signaling, are also provided. In one embodiment, a method includes administering an amount of an agent that reduces or inhibits OX40 or OX40L signaling, expression or activity sufficient to alleviate or ameliorate the symptom. In another embodiment, a method includes administering an amount of an agent that reduces or inhibits OX40 or OX40L signaling, expression or activity sufficient to reduce or inhibit one or more symptoms associated with a secondary or subsequent immune response. In yet another embodiment, a method includes administering an amount of an agent that reduces or inhibits an OX40 mediated T cell response sufficient to alleviate or ameliorate the symptom. In still another embodiment, a method includes administering an amount of an agent that reduces or inhibits an OX40 mediated T cell response sufficient to reduce or inhibit the OX40 mediated T cell response, thereby reducing or inhibiting one or more symptoms associated with a secondary or subsequent immune response.

Methods of treating asthma (e.g., mediated at least in part by OX40 signaling) are additionally provided. In one embodiment, a method includes administering to a subject having asthma an amount of an agent sufficient to reduce or inhibit OX40 or OX40L signaling, expression or activity, thereby treating asthma. In another embodiment, a method includes administering to a subject having asthma an amount of an agent sufficient to reduce or inhibit OX40 mediated T cell response, thereby treating asthma.

Methods of alleviating, ameliorating, reducing and inhibiting one or more symptoms of asthma (e.g., mediated at least in part by OX40 signaling) are further provided. In one embodiment, a method includes administering to a subject having asthma an amount of an agent sufficient to reduce or inhibit OX40 or OX40L signaling, expression or activity, thereby alleviating or ameliorating a symptom associated with asthma. In another embodiment, a method includes administering to a subject having or suspected of having asthma an amount of an agent sufficient to reduce or inhibit OX40 or OX40L signaling, expression or activity, thereby reducing or inhibiting one or more symptoms of asthma. In yet another embodiment, a method includes administering to a subject having or suspected of having asthma an amount of an agent sufficient to reduce or inhibit OX40 mediated T cell response, thereby reducing or inhibiting one or more symptoms of asthma.

Methods of inhibiting or reducing a recall response associated with asthma (e.g., mediated at least in part by OX40 signaling) caused at least in part by exposure to an antigen are provided. In one embodiment, a method includes administering to a subject having asthma an amount of an agent sufficient to reduce or inhibit OX40 or OX40L signaling, expression or activity, thereby inhibiting or reducing a recall response associated with asthma.

Methods of preventing asthma in a subject having asthma caused at least in part by exposure to an antigen are provided. In one embodiment, a method includes administering to the subject an amount of an agent sufficient to reduce or inhibit OX40 or OX40L signaling, expression or activity, thereby preventing asthma.

Methods of preventing a recall response associated with asthma in a subject having asthma caused at least in part by exposure to an antigen are also provided. In one embodiment, a method includes administering to the subject an amount of an agent sufficient to reduce or inhibit OX40 or OX40L signaling, expression or activity, thereby preventing a recall response associated with asthma.

Methods of decreasing inflammation (e.g., preventing or eliminating inflammation) associated with a memory response are further provided. In one embodiment, a method includes administering to a subject having inflammation associated with a memory response an amount of an agent sufficient to reduce or inhibit OX40 or OX40L signaling, expression or activity, thereby decreasing inflammation associated with a memory response.

Methods of decreasing a T cell inflammatory memory response (e.g., preventing or eliminating T cell inflammatory memory response) are moreover provided. In one embodiment, a method includes administering to a subject having inflammation associated with a memory response an amount of an agent sufficient to reduce or inhibit OX40 or OX40L signaling, expression or activity, thereby decreasing a T cell inflammatory memory response.

Subjects include mammalian subjects, such as humans. Subjects further include those having, at risk of having or whom have previously had a recall response, a symptom associated with a recall response, or have been diagnosed as susceptible to a recall response. Fore example, a subject having one or more symptoms of asthma (e.g., allergic asthma).

Symptoms include, for example, symptoms associated with inflammation such as swelling, enlargement, mucus production, rash, eosinophil infiltration, leukocyte or lymphocyte infiltration, cytokine or chemokine production, hyperplasia, inflammatory lesions or necrosis. Symptoms further include, for example, symptoms associated with asthma and allergic asthma such as, wheezing, shortness of breath, chest tightness, cough, and sputum production, airflow restriction, airway edema, mucus production, eosinophil infiltration of lung, leukocyte infiltration of lung, hyperplasia of mucus secreting epithelium, inflammatory lesion of lung, goblet cell hyperplasia, or increased Th2 cytokine (e.g., IL-4, IL-5, IL-9, IL-13 or IL-16) production.

Agents include, for example, molecules that bind to OX40 or OX40L (e.g., an antibody, human or humanized, or a modified OX40 or OX40L), OX40 and OX40L subsequences, variant sequences, chimeric sequences and dominant negative sequences; antisense nucleic acid molecules or RNAi that bind to OX40 or OX40L DNA or RNA. Agents further include cytokines (e.g., IL-10) and molecules that directly or indirectly modulate OX40/OX40L signaling, expression or activity.

Methods of identifying agents that reduce or inhibit a recall immune response, are provided. In one embodiment, a method includes: providing a test agent that reduces or inhibits signaling, expression or activity of OX40 or OX40 ligand (OX40L); and measuring a recall immune response in the presence of the test agent. In another embodiment, a method includes: providing a test agent that binds to OX40 or OX40 ligand (OX40L); and measuring a recall immune response in the presence of the test agent. A reduction or inhibition of a recall response identifies the test agent as an agent that reduces or inhibits a recall immune response.

Methods of identifying agents that alleviate or ameliorate a symptom associated with a secondary or subsequent immune response to an antigen are also provided. In one embodiment, a method includes: providing a test agent that reduces or inhibits signaling, expression or activity of OX40 or OX40 ligand (OX40L); and measuring a symptom associated with a secondary or subsequent immune response to an antigen in the presence of the test agent. In another embodiment, a method includes: providing a test agent that binds to OX40 or OX40 ligand (OX40L); and measuring a symptom associated with a secondary or subsequent immune response to an antigen in the presence of the test agent. A reduction or inhibition of a symptom associated with a secondary or subsequent immune response to an antigen identifies the test agent as an agent that alleviates or ameliorates a symptom associated with a secondary or subsequent immune response to an antigen. In various aspects, the recall immune response is mediated at least in part by OX40 signaling, occurs in vivo (e.g., in a mammal)

Test agents are selected from agents as set forth herein and include, for example, modified OX40 or OX40L, OX40 and OX40L subsequences, variant sequences, chimeric sequences and dominant negative sequences, antibodies (human or humanized) an antisense nucleic acid molecule or RNAi that binds to OX40 or OX40L DNA or RNA, cytokines, and molecules that directly or indirectly modulate OX40/OX40L signaling, expression or activity. Test agents further include libraries of compounds.

Methods of identifying agents that alleviate or ameliorate a symptom associated with asthma (e.g., mediated at least in part by OX40 signaling) are additionally provided. In one embodiment, a method includes: providing a test agent that reduces or inhibits signaling, expression or activity of OX40 or OX40 ligand (OX40L); and measuring a symptom associated with asthma in the presence of the test agent. In another embodiment, a method includes: providing a test agent that binds to OX40 or OX40 ligand (OX40L); and measuring a symptom associated with asthma in the presence of the test agent. A reduction or inhibition of a symptom associated with asthma identifies the test agent as an agent that alleviates or ameliorates a symptom associated with asthma.

Methods of identifying agents for treating asthma are provided. In one embodiment, a method includes: providing a test agent that reduces or inhibits signaling, expression or activity of OX40 or OX40 ligand (OX40L); and measuring asthma in the presence of the test agent. In another embodiment, a method includes: providing a test agent that binds to OX40 or OX40 ligand (OX40L); and measuring asthma in the presence of the test agent. Alleviating or ameliorating asthma identifies the test agent as an agent for treating asthma.

Figure 1:
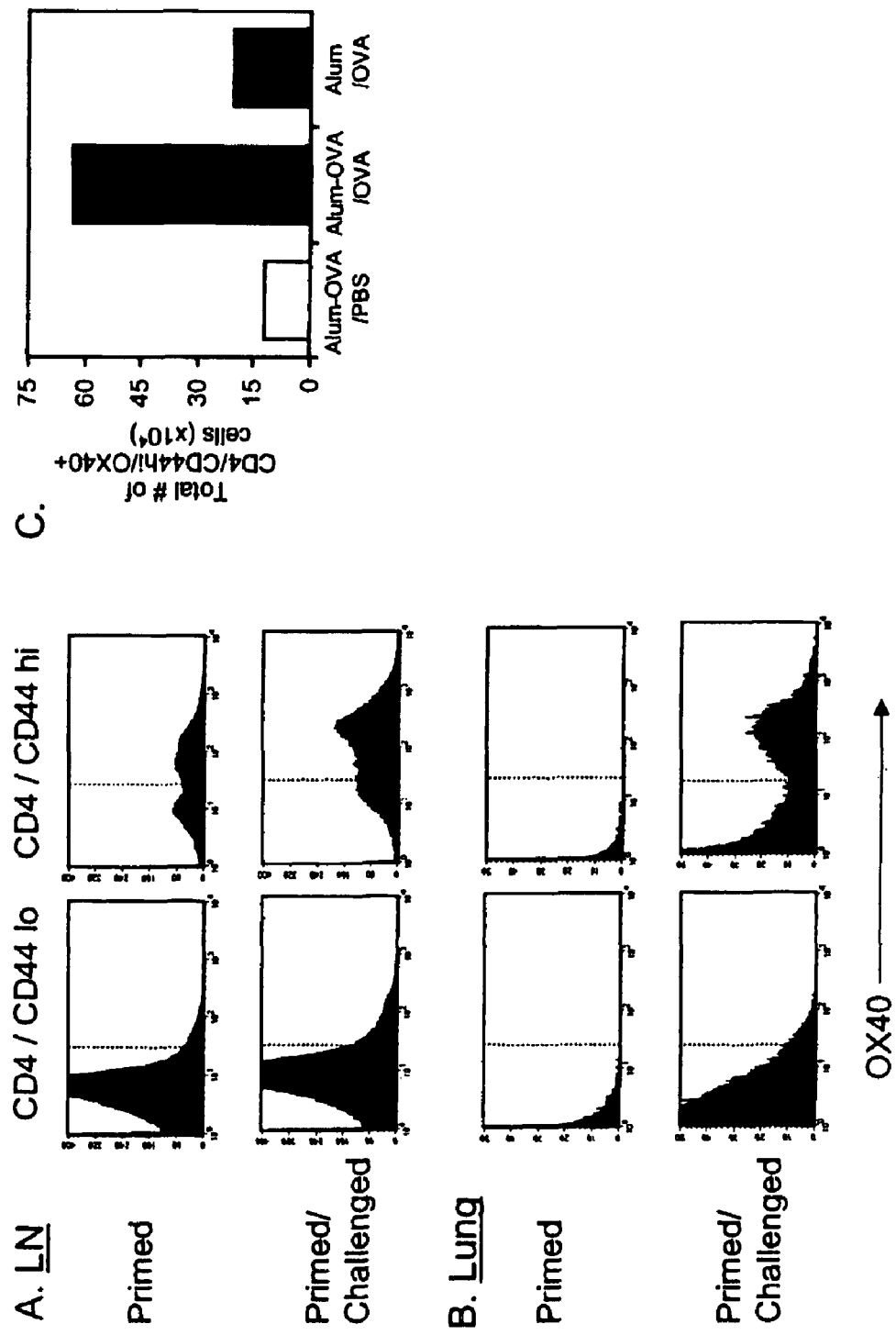
FIGS. 1A-1C show that OX40 is expressed on memory and memory effector T cells. (A) Peribronchial lymph nodes (LN) and (B) lung expression of OX40 on CD4/CD44lo or CD4/CD44hi T cells. (C) Total numbers of OX40 positive CD4/CD44hi T cells in lymph nodes from primed mice challenged with PBS (Alum-OVA/PBS), primed mice challenged with OVA (Alum-OVA/OVA), and unprimed mice challenged with OVA (Alum/OVA). Similar results were observed in 3 studies.

FIGS. 6A-6D show that primed OX40−/− T cells do not accumulate efficiently in recall responses in vivo. OVA-specific Th2 memory cells were generated in vitro as described in Example 7. After the last OVA challenge, (A, B) peribronchial lymph node, and (C, D) lung were analyzed for CD4 T cell (A, C) division, and (B, D) accumulation. Data are representative of 2 separate studies.

FIGS. 7A-7B show that primed OX40-deficient T cells cannot induce pronounced airway inflammation. OVA-specific Th2 memory cells were generated in vitro as described in Example 7. (A) Eosinophil numbers in BAL after the last OVA challenge. (B) IL-4, IL-5, and IL-13 levels in BAL with wt T cells challenged with PBS (Grp A), wt T cells challenged with OVA (Grp B), and OX40−/− T cells challenged with OVA (Grp C). Similar results were observed in three separate studies.

FIGS. 8A-8F show that OX40/OX40L interactions control both late secondary and tertiary recall responses to inhaled antigen. (A) Immunization Protocol A (Example 9) for secondary response of late memory T cells. Unprimed control mice with alum alone (Alum), primed mice with OVA adsorbed to alum (Alum-OVA). OVA challenge (days 60-64; indicated by arrows). PBS (Group A: Alum/OVA), control IgG (Group B: Alum-OVA/IgG-OVA) or anti-OX40L (Group C: Alum-OVA/RM134L-OVA) administered on each challenge day (indicated by filled symbols). (D) Immunization Protocol B (Example 9) for tertiary response of late memory T cells. Unprimed control mice with alum alone (Alum), primed mice with OVA adsorbed to alum (Alum-OVA). OVA challenge in a secondary response (days 25-29). Mice challenged in a tertiary response with OVA (days 120-124; indicated by arrows). PBS (Group A: Alum/OVA), control IgG (Group B: Alum-OVA/IgG-OVA) or anti-OX40L (Group C: Alum-OVA/RM134L-OVA) administered on each challenge day (indicated by filled symbols). (B, E) Total leukocyte, and (C, F) eosinophil numbers in BAL from mice in (B, C) Protocol A, and (E, F) Protocol B. Individual responses of 4 mice in each group are illustrated.

DETAILED DESCRIPTION

The invention is based at least in part on the discovery that antigen exposure markedly up-regulates OX40 expression on memory Th2 cells. Signaling through OX40 is critical for induction of inflammation in lung and mucosal immune responses. In addition, OX40/OX40 ligand (OX40L) signaling induces asthmatic-like reactions including airway hyperreactivity, mucus production, cytokine production and eosinophil infiltration. Thus, OX40/OX40L signaling during antigen recognition contributes to functional memory and recall immune response. T cells can therefore be regulated by OX40/OX40L and consequently, reducing, inhibiting or blocking OX40/OX40L signaling, expression or activity can reduce, inhibit or block a recall immune response, and one or more undesirable or adverse symptoms and physiological complications associated with recall immune response.

In accordance with the invention, there are provided methods of reducing, inhibiting and preventing a recall immune response to an antigen. In one embodiment, a method includes administering an amount of an agent sufficient to reduce or inhibit or prevent OX40 or OX40L signaling, expression or activity. In one aspect, the recall response is mediated at least in part by OX40 signaling (e.g., OX40 or OX40L). In another aspect, the recall response is associated with asthma (e.g., caused at least in part by exposure to an antigen). In various aspects, agents include, for example, a cytokine such as IL-10; a molecule that binds to OX40 or OX40L, such as modified OX40/OX40L (e.g., subsequence, variant, fusion or dominant negative) or OX40/OX40L antibodies; and OX40/OX40L nucleic acid including antisense and RNAi. In an additional aspect, the agent is administered to a mammalian subject (e.g., a human).

As used herein, "recall response," "recall immune response," "memory response," "memory immune response" and grammatical variations thereof means an immune response to an antigen to which a subject has previously been exposed. A recall or memory response is therefore an immune response subsequent to the initial antigen exposure and immune response. For example, a recall response may occur following exposure of the subject to the antigen for a second (secondary), third (tertiary), fourth, fifth, sixth, seventh, eighth, ninth, tenth, or any subsequent antigen exposure.

A recall or memory response is distinguished from a primary response to an antigen; a primary response is an immune response that occurs when a subject is exposed to an antigen for the first time. In a primary response, naïve T cells expand. In contrast, recall immune responses are believed to be attributed to reactivation of long-lived, antigen-primed T lymphocytes that arise from differentiated effector T cells in a quiescent state. Thus, a "recall response" is an immune response in which antigen-primed Th2 cells participate.

In the case of allergens, the primary immune response is a T-helper cell type 2 (Th2) response, which occurs prenatally. During the early years of life the immune system matures, which is primarily determined by genetic susceptibility but also influenced by exposure to allergens and infections. The development of an allergy results from repeated antigen exposure and an inappropriate response to environmental signals that result in an inability to dampen Th2 memory responses.

In the particular example of allergic asthma, the response can be considered in two-stages. The first involves the development of allergen-specific immunological memory against inhaled allergens, which happens during childhood and polarizes the immune response towards a Th2 phenotype making individuals more prone to developing allergic inflammation. The second involves consolidation and maintenance of this polarized Th2 response, leading to a state of chronic airway inflammation.

In the case of viruses and bacteria, the immune response is a Th1 response. Th1 recall responses occur upon secondary or subsequent exposure to the viral or bacterial antigen. Th1 responses are associated with the production of different cytokines, such as IFNγ, TNF, IL-2 and IL-12. Immune cells that participate in Th1 responses include neutrophils and macrophages. Th1 recall responses occur in various organs and tissues, including lung, upon secondary or subsequent exposure to viral or bacterial antigen.

Recall immune responses can result in undesirable or adverse symptoms and physiological complications, such as inflammation. Because OX40/OX40L signaling participates in recall response, modulating (increasing or decreasing) OX40/OX40L signaling, expression or activity provides a means with which to modulate one or more symptoms (i.e., undesirable or adverse symptoms) and physiological complications associated with recall responses (e.g., allergic responses).

Thus, the invention provides methods of alleviating or ameliorating one or more symptoms (i.e., undesirable or adverse symptoms) and physiological complications associated with a secondary or subsequent immune response, and methods of alleviating or ameliorating one or more symptoms (i.e., undesirable or adverse symptoms) and physiological complications associated with a secondary or subsequent immune response. In one embodiment, a method includes administering an amount of an agent sufficient to reduce or inhibit or prevent OX40 or OX40L signaling, expression or activity, thereby alleviating or ameliorating one or more symptoms associated with a secondary or subsequent immune response (e.g., inflammation). In one aspect, the secondary or subsequent immune response is mediated at least in part by OX40 signaling (e.g., OX40 or OX40L). In various additional aspects, agents include, for example, a cytokine such as IL-10; a molecule that binds to OX40 or OX40L, such as modified OX40/OX40L (e.g., subsequence, variant, fusion or dominant negative) or an OX40/OX40L antibody; and an OX40/OX40L nucleic acid including antisense and RNAi.

Further provided are methods of reducing, inhibiting and preventing one or more symptoms associated with a secondary or subsequent immune response to an antigen.

In one embodiment, a method includes administering an amount of an agent sufficient to reduce or inhibit or prevent OX40/OX40L signaling, expression or activity to reduce or inhibit or prevent one or more symptoms of associated with a secondary or subsequent immune response to an antigen. In another embodiment, a method includes administering an amount of an agent sufficient to reduce or inhibit or prevent OX40 mediated T cell response, thereby reducing or inhibiting or preventing one or more symptoms associated with a secondary or subsequent immune response. In one aspect, OX40 mediated T cell response contributes to inflammation.

As used herein, the term "OX40 mediated T cell response," means that OX40 or OX40L signaling, expression or activity stimulates or induces recall response in which antigen experienced (memory) Th2 cells participate. This T cell response can in turn contribute to inter alia, inflammation, cytokine production (associated with Th2 cells), and effector cell infiltration of the affected region of the organ or tissue.

Additionally provided are methods of reducing, inhibiting and preventing one or more symptoms (i.e., undesirable or adverse symptoms) of asthma. In one embodiment, a method includes administering to a subject having or suspected of having asthma an amount of an agent sufficient to reduce, inhibit or prevent OX40 or OX40L expression or activity, thereby reducing, inhibiting or preventing one or more symptoms of asthma. In another embodiment, a method includes administering to a subject having or suspected of having asthma an amount of an agent sufficient to reduce, inhibit or prevent an OX40 mediated T cell response, thereby reducing, inhibiting or preventing one or more symptoms of asthma. In one aspect, OX40 mediated T cell response contributes to inflammation. In another aspect, the symptom is caused at least in part by exposure to an antigen, e.g., a secondary or subsequent exposure.

The invention therefore further provides methods of treating and preventing asthma. In one embodiment a method includes administering to a subject having asthma an amount of an agent sufficient to reduce or inhibit or prevent OX40 or OX40L expression or activity, thereby treating or preventing asthma. In another embodiment, a method includes administering to a subject having asthma an amount of an agent sufficient to reduce or inhibit or prevent OX40 or OX40L signaling, expression or activity, thereby alleviating or ameliorating a symptom associated with asthma. In yet another embodiment, a method includes administering to a subject having asthma an amount of an agent sufficient to reduce or inhibit or prevent an OX40 mediated T cell response, thereby treating asthma. Particular aspects include acute asthmatic episodes or chronic asthma, for example, a subject that exhibits one or more mild, moderate or severe symptoms (i.e., undesirable or adverse symptoms) or physiological complications associated with or caused by asthma. In another aspect, asthma is allergic asthma.

Undesirable or adverse symptoms and physiological complications alleviated or ameliorated in a method of the invention include any undesirable or adverse affect associated with or caused by a recall immune response, such as symptoms associated with an allergic reaction. Particular non-limiting examples include swelling (edema), enlargement, mucus production, dermatitis (rash), eosinophil infiltration of tissue or organ, leukocyte or lymphocyte infiltration of tissue or organ, undesirable cytokine or chemokine production (e.g., Th2 cytokine overproduction), tissue or organ hyperplasia, inflammatory lesions or necrosis of affected region of tissue or organ.

Methods of the invention include any cell type, tissue or organ affected by a recall immune response. Specific non-limiting examples include pulmonary tissue (lung), respiratory tract (larynx, trachea, bronchial tree, nasal cavity, paranasal sinuses, nasopharynx and pharynx), spleen, lymph nodes and lymphatic vessels (e.g., gut-associated lymph), cardiac (heart) tissue, and dermal tissue (skin).

Methods of the invention include any allergic disease or immune response affecting any cell type, tissue or organ. For example, an allergic disease or immune response associated with a recall response mediated, at least in part, by OX40/OX40L signaling. Specific non-limiting examples include allergic asthma, allergic rhinitis, atopic dermatitis, and gastro-intestinal allergies.

In lung, symptoms alleviated or ameliorated in a method of the invention include one or more symptoms associated with asthma, such as airway (upper or lower) hyper-reactivity (AHR)—wheezing, shortness of breath, chest tightness, cough, and sputum production, airflow obstruction/restriction (mild, moderate or severe bronchoconstriction), airway edema and mucus production. At the cellular level, symptoms that can be alleviated include eosinophil infiltration of lung, leukocyte infiltration of lung, hyperplasia of mucus secreting epithelial cells, inflammatory lesions of lung, goblet cell hyperplasia, and undesirable or increased Th2 cytokine production (e.g., IL-4, IL-5, IL-9, IL-13 and IL-16).

In nasopharynx, pharynx and sinuses, symptoms alleviated or ameliorated in a method of the invention include one or more symptoms of allergic rhinitis (AR), otitis media, abnormal facial development, orthodontic problems, eustachian tube dysfunction and sinusitis. AR is also associated with asthma and, as such, one or more symptoms of AR can be alleviated or ameliorated in accordance with the invention.

In spleen, symptoms alleviated or ameliorated in a method of the invention include enlargement (splenomegaly), hypersplenism, hyperplasia, fibrosis, abscesses and rupture.

In lymph node, symptoms alleviated or ameliorated in a method of the invention include swelling (lymphedema), enlargement, and neo-organogenesis.

In heart, symptoms alleviated or ameliorated in a method of the invention include one or more symptoms of a cardiomyopathy (myocarditis, hypertrophy, dilation and contractile dysfunction).

In skin, symptoms alleviated or ameliorated in a method of the invention include one or more symptoms of dermatitis (irritant and allergic types). Dermatitis (topic) or eczema can be manifested by itching erythema, papules, and vesicles in acute phase, and dryness, hyperkeratosis, and fissures in chronic phase. Eczematous lesions are characterized by a mononuclear infiltrate consisting mainly of T cells in the dermis and epidermis. Infiltrating T cells eventually cause keratinocyte apoptosis.

Assays for detecting the presence and severity of symptoms include, for example, measuring AHR and flow cytometry (Example 1), histological analysis (Example 4), IgE and Th2 cytokine production (Examples 1 and 5), and T cell accumulation in the affected organ or tissue (Example 6). Additional assays are known in the art and include, for example, lung function (LF), skin test or blood test for allergen-specific IgEs by radioallergosorbent (RAST), atopy patch test (APT) and skin prick test (SPT) techniques, total serum IgE, screening of basophil activation (BAT or FAST), assays for leukotriene LTC4 release (CAST), measurement of plasma histamine, serum tryptase, serum ECP, urinary EDN, assay of fecal IgEs, IgG precipitins for organic dusts. Other tests are known in the art (see, e.g., Volcheck G W, Postgrad Med. (2001) 109:71-2, 77-8, 84-5; Basketter et al., Food Chem Toxicol. (2001) 39:621; Steiling et al., Food Chem Toxicol. 2001 39:293; and Passali and Bellussi, Allergy. (1997) 52(33 Suppl):22).

As used herein, the term "ameliorate" or "alleviate," when used in reference to an undesirable or adverse symptom or complication (physiological or psychological), means a detectable or measurable therapeutic benefit to a subject. A therapeutic benefit is any objective or subjective transient or temporary, or longer term improvement in the subject's physiological or psychological condition. For example, a satisfactory clinical endpoint is achieved when there is an incremental improvement in the subjects condition, or a reduction or stabilization (inhibiting a progression or worsening of the condition) of the frequency, severity or duration of one or more undesirable or adverse symptoms (i.e., undesirable or adverse symptoms) or a physiological or psychological complication associated with or caused by the condition, or a stabilization, inhibition or reversal of one or more of the physiological, biochemical or cellular manifestations or characteristics associated with or caused by the condition.

To ameliorate or alleviate one or more symptoms and complications associated with a recall immune response therefore includes any reduction, inhibition, stabilization or prevention of an undesirable or adverse symptom or physiological or psychological complication associated with or caused by a recall immune response. Thus, "ameliorate" and "alleviate" does not require complete ablation of all undesirable or adverse symptoms or physiological or psychological complications associated with or caused by a recall response. For example, in the case of asthma, inhibiting or reducing the severity or incidence (frequency) of acute asthmatic episodes provides a therapeutic benefit (e.g., less frequent bouts or a reduction from moderate to mild asthmatic episodes) even though complete ablation of asthma may not result. An improvement in a subjects' subjective feeling, such as increased confidence, reduced depression, increased participation in outdoor or physical activities, and improved psychological well being, are also examples of a therapeutic benefit.

The term "sufficient," when used in reference to "amount" means the quantity effective to produce the desired effect, for example, a "therapeutic effect." Thus, for example, a "sufficient amount" will be effective to inhibit, reduce, or prevent, one or more of the undesirable or adverse symptoms and complications associated with a recall immune response.

The doses or "sufficient amount" to achieve a therapeutic benefit or improvement in a subject's condition are effective to alleviate or ameliorate one, several or all adverse symptoms or complications of the condition, to a measurable extent, although reducing, inhibiting or preventing progression or a worsening of the condition or an adverse symptom, is a satisfactory outcome. The dose may be proportionally increased or reduced as indicated by the status of the disease being treated or the side effects of the treatment. Doses also considered sufficient are those that result in a reduction of the use of another therapeutic regimen or protocol. For example, an OX40 or OX40L signaling antagonist is considered as having a therapeutic effect if administration of the antagonist results in reducing the frequency or dosage of a different treatment used to inhibit or reduce undesirable or adverse symptoms or complications of the condition.

As used herein, the term "signal" or "signaling," when used in reference to OX40 or OX40L, refers to an activity or function of OX40 or OX40L. An exemplary biological function is mediating a recall response, e.g., a Th2 recall response. Signaling of OX40 or OX40L can be modulated directly, by increasing or decreasing an OX40 or OX40L activity or function; or indirectly, by altering expression of OX40 or OX40L, or by altering expression or activity of another molecule(s) which in turn modulates an OX40 or OX40L activity or function, or expression of OX40 or OX40L.

Molecules that modulate OX40 or OX40L signaling include compounds that bind to OX40 or OX40L such as small organic compounds (e.g., drugs), polypeptide sequences (e.g., OX40/OX40L antibodies), and modified forms of OX40/OX40L (e.g., soluble, variant, fusion, mimetic, or dominant negative forms of OX40/OX40L). Molecules that modulate OX40 or OX40L signaling also include nucleic acid sequences. Molecules that modulate OX40 or OX40L signaling include compounds that modulate expression or activity of another molecule(s) which in turn modulates an OX40 or OX40L activity or function, or expression of OX40 or OX40L.

"Antibodies" refer to mammalian, human, humanized or primatized forms of heavy or light chain, $V_H$ and $V_L$, respectively, immunoglobulin (Ig) molecules. "Antibody" means any monoclonal or polyclonal immunoglobulin molecule, such as IgM, IgG, IgA, IgE, IgD, and any subclass thereof. The term "antibody" includes intact immunoglobulin molecules, two full length heavy chains linked by disulfide bonds to two full length light variable domains, $V_H$ and $V_L$, individually or in any combination, as well as fragments of immunoglobulins, such as Fab, Fab', (Fab')$_2$, Fv, Fd, scFv and sdFv, unless otherwise expressly stated.

An OX40 or OX40L antibody means an antibody that specifically binds to OX40 or OX40L. As used herein, the term "bind" or "binding" means that the compositions referred to have affinity for each other. "Specific binding" is where the binding is selective between two molecules. Thus, specific binding of an antibody for OX40 or OX40L is that which is selective for an epitope present in OX40 or OX40L. Typically, specific binding can be distinguished from non-specific when the dissociation constant ($K_D$) is less than about $1 \times 10^{-5}$ M or less than about $1 \times 10^{-6}$ M or $1 \times 10^{-7}$ M. Selective binding can be distinguished from non-selective binding using assays known in the art (e.g., immunoprecipitation, ELISA, Western blotting) with appropriate controls.

Monoclonal antibodies are made by methods known in the art (Kohler et al., Nature, 256:495 (1975); and Harlow and Lane, *Using Antibodies: A Laboratory Manual*, Cold Spring Harbor Laboratory, 1999). Briefly, monoclonal antibodies can be obtained by injecting mice with antigen (for example, intact polypeptide or peptide fragments of OX40/OX40L). The polypeptide or peptide used to immunize an animal may be derived from translated DNA or chemically synthesized and conjugated to a carrier protein. Commonly used carriers which are chemically coupled to the immunizing peptide include, for example, keyhole limpet hemocyanin (KLH), thyroglobulin, bovine serum albumin (BSA), and tetanus toxoid. Antibody production is verified by analyzing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from hybridoma cultures. Monoclonal antibodies can be isolated and purified from hybridoma cultures by a variety of established techniques which include, for example, affinity chromatography with Protein-A Sepharose, size-exclusion chromatography, and ion-exchange chromatography (see e.g., Coligan et al., *Current Protocols in Immunology* sections 2.7.1-2.7.12 and sections 2.9.1-2.9.3; and Barnes et al., "Methods in Molecular Biology," 10:79-104, Humana Press (1992)).

A "human antibody" means that the amino acid sequence of the antibody is fully human, i.e., human heavy and light chain variable and constant regions. The antibody amino acids are coded for in the human DNA antibody sequences or exist in a human antibody. An antibody that is non-human may be made fully human by substituting non-human amino acid residues with amino acid residues that exist in a human antibody. Amino acid residues present in human antibodies, CDR region maps and human antibody consensus residues are known in the art (see, e.g., Kabat, *Sequences of Proteins of Immunological Interest*, 4$^{th}$ Ed. US Department of Health and Human Services. Public Health Service (1987); Chothia and Lesk, J. Mol. Biol. (1987) 186:651; Padlan Mol. Immunol. (1994) 31:169; and Padlan Mol. Immunol. (1991) 28:489). Methods of producing human antibodies are known in the art (see, for example, WO 02/43478 and WO 02/092812).

The term "humanized," when used in reference to an antibody, means that the antibody sequence has non-human amino acid residues of one or more complementarity determining regions (CDRs) that specifically bind to the antigen in an acceptor human immunoglobulin molecule, and one or more human amino acid residues in the Fv framework region (FR) that flank the CDRs. Any mouse, rat, guinea pig, goat, non-human primate (e.g., ape, chimpanzee, macaque, orangutan, etc.) or other animal antibody may be used as a CDR donor for producing humanized antibody. Human framework region residues can be replaced with corresponding non-human residues. Residues in the human framework regions can therefore be substituted with a corresponding residue from the non-human CDR donor antibody. A humanized antibody may include residues, which are found neither in the human antibody nor in the donor CDR or framework sequences. The use of antibody components derived from humanized monoclonal antibodies reduces problems associated with the immunogenicity of non-human regions. Methods of producing humanized antibodies are known in the art (see, for example, U.S. Pat. Nos. 5,225,539; 5,530,101, 5,565,332 and 5,585,089; Riechmann et al., (1988) Nature 332:323; EP 239,400; WO91/09967; EP 592,106; EP 519, 596; Padlan Molecular Immunol. (1991) 28:489; Studnicka et al., Protein Engineering (1994) 7:805; Singer et al., J. Immunol. (1993) 150:2844; and Roguska et al., Proc. Nat'l. Acad. Sci. USA (1994) 91:969).

"Primatized" antibodies are within the meaning of "humanized" as used herein, except that the acceptor human immunoglobulin molecule and framework region amino acid residues may be any primate residue (e.g., chimpanzee, ape, orangutan, gibbon, etc.), in addition to any human residue.

A specific example of an OX-40 antibody is OX-40-specific monoclonal antibody OX-86 (al-Shamkhani et al., Eur J Immunol. (1996) 26:1695; Rogers and Croft, J. Immunol. (2000) 164:2955; and Kjaergaard et al., J Immunol. (2001) 167:6669). Specific examples of OX-40- and OX40L-specific antagonist and agonist antibodies are also known in the art: antagonist anti-mouse OX40L antibody RM134L (Example 1 and Akiba et al., J. Immunol. (1999) 162:7058); antagonist anti-human OX40L (gp34) antibody ik-1 (Matsumura et al., J Immunol. (1999) 163:3007); antagonist anti-rat OX40L ATM-2 (Satake et al., Biochem Biophys Res Commun. (2000) 270:1041) and agonistic anti-OX40 antibody (Pan et al., Mol Ther. (2002) 6:528).

As used herein, the terms "peptide," "polypeptide" and "protein" are used interchangeably and refer to two or more amino acids covalently linked by an amide bond or non-amide equivalent. Polypeptides include full length native polypeptide, and "modified" forms such as subsequences, variant sequences, fusion/chimeric sequences and dominant-negative sequences. Specific non-limiting examples of polypeptides include antibodies and forms of OX40 and OX40L having antagonistic and agonistic activity on OX40/OX40L signaling.

Peptides include L- and D-isomers, and combinations thereof. Peptides can include modifications typically associated with post-translational processing of proteins, for example, cyclization (e.g., disulfide or amide bond), phosphorylation, glycosylation, carboxylation, ubiquitination, myristylation, or lipidation. Modified peptides can have one or more amino acid residues substituted with another residue, added to the sequence or deleted from the sequence. Specific examples include one or more amino acid substitutions, additions or deletions (e.g., 1-3, 3-5, 5-10, 10-20, or more).

Subsequences and fragments refer to polypeptides having one or more fewer amino acids in comparison to a reference (e.g., native) polypeptide sequence. A recombinant soluble OX40 subsequence can have agonist activity (Kotani et al., Immunol Lett. 2002 84:1) or antagonist activity. An antibody subsequence that specifically binds to OX40 or OX40L can retain at least a part of its binding or agonist or antagonist function.

A variant peptide can have a sequence with 50%, 60%, 70%, 75%, 80%, 85%, 90%, 95%, 96%, 97%, 98%, or more identity to a reference sequence (e.g., OX40/OX40L or an antibody that binds to OX40/OX40L). Variant sequences include naturally occurring alterations of sequence, due to intra-species polymorphisms or different species, as well as artificially produced alterations of sequence. Sequence homology between species is in the range of about 70-80%. An amino acid substitution is one example of a variant.

A "conservative substitution" is the replacement of one amino acid by a biologically, chemically or structurally similar residue. Biologically similar means that the substitution is compatible with an activity or function of the unsubstituted sequence. Structurally similar means that the amino acids have side chains with similar length, such as alanine, glycine and serine, or having similar size. Chemical similarity means that the residues have the same charge or are both hydrophilic or hydrophobic. Particular examples include the substitution of one hydrophobic residue, such as isoleucine, valine, leucine or methionine for another, or the substitution of one polar residue for another, such as the substitution of arginine for lysine, glutamic for aspartic acids, or glutamine for asparagine, serine for threonine, and the like.

Peptides synthesized and expressed as fusion proteins have one or more additional domains linked thereto, and are also referred to as chimeric polypeptides. The additional domain (s) may confer an additional function upon the sequence. For example, OX40-IgG fusion proteins can have antagonistic activity (Taylor et al., J Leukoc Biol. (2002) 72:522) or agonist activity.

The term "fusion," when used in reference to two or more molecules (e.g., polypeptides) means that the molecules are covalently attached. A particular example for attachment of two protein sequences is an amide bond or equivalent. The term "chimeric," and grammatical variations thereof, when used in reference to a protein, means that the protein is comprised of one or more heterologous amino acid residues from one or more different proteins.

The term "heterologous," when used in reference to a polypeptide, means that the polypeptide is not normally contiguous with the other polypeptide in its natural environment. Thus, a chimeric polypeptide means that a portion of the polypeptide does not exist fused with the other polypeptide in normal cells. In other words, a chimeric polypeptide is a molecule that does not normally exist in nature, i.e., such a molecule is produced by the hand man, e.g., artificially produced through recombinant DNA technology.

As used herein, the term "mimetic" refers to a synthetic chemical compound which has substantially the same structural and/or functional characteristics as the reference molecule. The mimetic can be entirely composed of synthetic, non-natural amino acid analogues, or can be a chimeric molecule including one or more natural peptide amino acids and one or more non-natural amino acid analogs. The mimetic can also incorporate any number of natural amino acid conservative substitutions as long as such substitutions do not destroy activity. As with polypeptides which are conservative variants, routine testing can be used to determine whether a mimetic modulates OX40/OX40L signaling.

Peptide mimetics can contain any combination of non-natural structural components, which are typically from three structural groups: a) residue linkage groups other than the natural amide bond ("peptide bond") linkages; b) non-natural residues in place of naturally occurring amino acid residues; or c) residues which induce secondary structural mimicry, i.e., induce or stabilize a secondary structure, e.g., a beta turn, gamma turn, beta sheet, alpha helix conformation, and the like. For example, a polypeptide can be characterized as a mimetic when one or more of the residues are joined by chemical means other than an amide bond. Individual peptidomimetic residues can be joined by amide bonds, non-natural and non-amide chemical bonds other chemical bonds or coupling means including, for example, glutaraldehyde, N-hydroxysuccinimide esters, bifunctional maleimides, N,N'-dicyclohexylcarbodiimide (DCC) or N,N'-diisopropylcarbodiimide (DIC). Linking groups alternative to the amide bond include, for example, ketomethylene (e.g., —C(=O)—CH$_2$— for —C(=O)—NH—), aminomethylene (CH$_2$—NH), ethylene, olefin (CH=CH), ether (CH$_2$—O), thioether (CH$_2$—S), tetrazole (CN$_4$—), thiazole, retroamide, thioamide, or ester (see, e.g., Spatola (1983) in *Chemistry and Biochemistry of Amino Acids, Peptides and Proteins*, Vol. 7, pp 267-357, "Peptide and Backbone Modifications," Marcel Decker, NY).

Peptides and peptidomimetics can be produced and isolated using a variety of methods known in the art. Full length peptides and fragments (subsequences) can be synthesized using chemical methods known in the art (see, e.g., Caruthers, Nucleic Acids Res. Symp. Ser. (1980) 215; Horn, Nucleic Acids Res. Symp. Ser. (1980) 225; and Bongo, A. K., Therapeutic Peptides and Proteins, Formulation, Processing and Delivery Systems (1995) Technomic Publishing Co., Lancaster, Pa.). Peptide synthesis can be performed using various solid-phase techniques (see, e.g., Roberge, Science (1995) 269:202; Merrifield, Methods Enzymol. (1997) 289:3). Automated synthesis may be achieved, e.g., using the ABI 431A Peptide Synthesizer (Perkin Elmer) in accordance with the manufacturer's instructions.

Individual synthetic residues and polypeptides incorporating mimetics can be synthesized using a variety of procedures and methodologies known in the art (see, e.g., Organic Syntheses Collective Volumes, Gilman, et al. (Eds) John Wiley & Sons, Inc., NY). Peptides and peptide mimetics can also be synthesized using combinatorial methodologies. Techniques for generating peptide and peptidomimetic libraries are known, and include, for example, multipin, tea bag, and split-couple-mix techniques (see, for example, al-Obeidi, Mol. Biotechnol. (1998) 9:205; Hruby, Curr. Opin. Chem. Biol. (1997) 1:114; Ostergaard, Mol. Divers. (1997) 3:17; and Ostresh, Methods Enzymol. (1996) 267:220). Modified peptides can be further produced by chemical modification methods (see, e.g., Belousov, Nucleic Acids Res. (1997) 25:3440; Frenkel, Free Radic. Biol. Med. (1995) 19:373; and Blommers, Biochemistry (1994) 33:7886).

OX40/OX40L nucleic acids including antisense and RNAi can modulate expression of OX40/OX40L. Antisense includes single, double or triple stranded polynucleotides and peptide nucleic acids (PNAs) that bind RNA transcript or DNA. For example, a single stranded nucleic acid can target OX40 or OX40L transcript (e.g., mRNA). Oligonucleotides derived from the transcription initiation site of the gene, e.g., between positions −10 and +10 from the start site, are a particular one example. Triplex forming antisense can bind to double strand DNA thereby inhibiting transcription of the gene. "RNAi" is the use of double stranded RNA sequences for inhibiting gene expression (see, e.g., Kennerdell et al., (1998) Cell 95:1017; and Fire et al., (1998) Nature, 391:806). Double stranded RNA sequences from an OX40 or OX40L coding region may therefore be used to inhibit or prevent OX40 or OX40L expression.

Antisense and RNAi can be produced based upon the OX40 and OX40L sequences known in the art. OX40 sequences are described, for example, in Latza et al. (Eur J Immunol. (1994) 24:677, human OX40), and Birkeland et al. (Eur J Immunol. (1995) 25:926, mouse OX40). OX40L sequences are described, for example, in Godfrey et al. (J Exp Med. (1994) 180:757, human OX-40L), Baum et al. (EMBO J. (1994) 13:3992, mouse OX40L), and Akiba et al. (Biochem Biophys Res Commun. (1998) 251:131, rat OX40L).

Molecules that directly or indirectly modulate expression of OX40/OX40L further include cytokines such as include IL-10, which reduces OX40/OX40L signaling, and IL-1 and IL-4, which induce expression of OX40 on T cells (Nakae et al. J Immunol. (2001) 167:90; and Iwakura Y, Cytokine Growth Factor Rev. (2002) August-October; 13(4-5):341). CD28 also induces OX40 expression. CD40 and Toll-like receptor (TLR) agonists increase OX40L expression. Thus, molecules that can be employed in order to reduce or inhibit OX40/OX40L signaling in accordance with the invention include IL-10, and molecules that inhibit IL-4, CD28, CD40, TLR expression or activity (e.g., antibodies or antagonists that bind IL-4, CD28, CD40, or TLR).

Dominant negative molecules that can directly or indirectly modulate OX40/OX40L signaling include dominant negative TRAF (tumor necrosis factor receptor (TNFR) associated factors) family members, Akt (Protein Kinase B), JNK (Jun N-terminal Kinase), and IKK (I kappa B Kinase) molecules (Kawamata et al., J. Biol. Chem (1998) 273:5808; Kelly et al., J. Immunol. (2002) 168:597; Rincon et al., J. Exp. Med. (1998) 188:1817; and Harhaj and Sun, J. Biol. Chem. (1998) 273:25185).

Excluded agents from the methods of the invention are agents that are known in the art and that function to reduce or inhibit a recall immune response (e.g., Th2 recall response) by inhibiting OX40/OX40L signaling, and that have been used for that purpose. Thus, agents known in the art and that have been used to treat a recall immune response associated with allergic asthma, for example, if they function by reducing, inhibiting or preventing OX40/OX40L signaling, are excluded from the invention in vitro, ex vivo or in vivo methods.

Agents that may be excluded include one or more of the following: budesonide, prednisone, flunisolide, flunisolide hydrofluoroalkane, estrogen, progesterone, dexamethasone, loteprednol, bambuterol, formoterol, salmeterol, albuterol, ipratropium bromide, oxitropium bromide, cromolyn, terfenadine, astemizole, hydroxyzine, chlorpheniramine, tripelennamine, cetirizine, desloratadine, mizolastine, fexofenadine, olopatadine hydrochloride, norastemizole, levocetirizine, levocabastine, azelastine, ebastine, loratadine, oxatomide, montelukast, zafirlukast, zileuton, ibudilast, cilomilast, BAY 19-8004, theophylline, doxofylline, seratrodast, ozagrel hydrochloride, ramatroban, celecoxib and rofecoxib.

Invention methods include treatment protocols and therapeutic regimens or strategies alone, and in combination with each other. For example, any treatment protocol or therapeutic regimen or strategy that inhibits, reduces or prevents a recall response, or reduces the likelihood that a recall response will occur, can be used to reduce or inhibit a recall immune response alone, or in combination with another treatment protocol or therapeutic regimen. Such treatments include compounds, agents, therapies and treatments having an immune-inhibiting or immune-reducing activity or function. The term "immune-response inhibiting," or "immune-response reducing" when used in reference to such a compound, agent, therapy or treatment, means that the compound, agent, therapy or treatment decreases, prevents, an immune response that is humoral or cell-mediated.

Particular non-limiting examples of agents useful for treating inflammation (e.g., asthma) include immunosuppressive agents such as corticosteroids (steroid receptor agonists) including budesonide, prednisone, flunisolide, flunisolide hydrofluoroalkane, estrogen, progesterone, dexamethasone and loteprednol; beta-agonists (e.g., short or long-acting) such as bambuterol, formoterol, salmeterol, albuterol; anticholinergics such as ipratropium bromide, oxitropium bromide, cromolyn and calcium-channel blocking agents; antihistamines such as terfenadine, astemizole, hydroxyzine, chlorpheniramine, tripelennamine, cetirizine, desloratadine, mizolastine, fexofenadine, olopatadine hydrochloride, norastemizole, levocetirizine, levocabastine, azelastine, ebastine and loratadine; antileukotrienes (e.g., anti-cysteinyl leukotrienes (CysLTs)) such as oxatomide, montelukast, zafirlukast and zileuton; phosphodiesterase inhibitors (e.g., PDE4 subtype) such as ibudilast, cilomifast, BAY 19-8004, theophylline (e.g., sustained-release) and other xanthine derivatives (e.g., doxofylline); thromboxane antagonists such as seratrodast, ozagrel hydrochloride and ramatroban; prostaglandin antagonists such as COX-1 and COX-2 inhibitors (e.g., celecoxib and rofecoxib), aspirin; and potassium channel openers.

Additional specific examples of anti-inflammatory agents include antibodies, receptors or receptor ligands, such as anti-IgE (e.g., rhuMAb-E25 omalizumab), -IgA and -IgG antibodies; antibodies and soluble receptors against cytokines such as IL-1, IL-4, IL-5, IL-9, IL-13 and IL-16 or growth factors such as granulocyte/macrophage colony-stimulating factor; cytokines such as IL-10; mucolytics (depolymerize polymers of mucin or DNA/actin, or increase cough clearance) such as ambroxol and N-acetylcysteine; expectorants; and allergens (allergan immunotherapy).

Treatment strategies include avoidance of triggers (environmental or food allergan avoidance) and self-management.

Invention methods include applications in vitro, ex vivo and in vivo, i.e., in a subject. The term "subject," also referred to as "patient," as used herein means an animal, such as a non-mammal or mammalian (e.g., primate, human) organism. Subjects further include animal models in which a recall immune response is directly or indirectly involved in an undesirable or adverse symptom or physiological or psychological complication or condition.

Candidate subjects and patients include any subject having or at risk of having a recall response. Specific examples include subjects with a history of having an undesirable or adverse recall response, or an undesirable or adverse symptom or physiological or psychological complication or condition associated or caused by a recall response. Another example is a subject who has not been diagnosed with an undesirable or adverse recall response, or complication associated or caused by a recall response, but who is suspected of having a recall response. For example, a subject may be suspected of having asthma, but has not yet been diagnosed with asthma. Such subjects, suspected of having a recall response, are appropriate candidate subjects. Additional specific non-limiting examples are described herein, such as acute or chronic asthma (e.g., allergic), and are also known in the art.

Agents and compounds useful in the methods of the invention can be formulated into a pharmaceutically acceptable carrier or diluent using known techniques. The pharmaceutically acceptable carrier or diluent can be selected based upon the amount of active ingredient with which it is to be combined, the route of administration and other known variables.

Pharmaceutical compositions include "pharmaceutically acceptable" and "physiologically acceptable" carriers, diluents or excipients. The terms "pharmaceutically acceptable" and "physiologically acceptable," when referring to carriers, diluents or excipients includes solvents (aqueous or non-aqueous), detergents, solutions, emulsions, dispersion media, coatings, isotonic and absorption promoting or delaying agents, compatible with pharmaceutical administration and with the other components of the formulation. Such formulations further include a tablet (coated or uncoated), capsule (hard or soft), microbead, emulsion, powder, granule, crystal, suspension, syrup or elixir.

Pharmaceutical compositions can be formulated to be compatible with a particular route of administration. Compositions for parenteral, intradermal, or subcutaneous administration can include a sterile diluent, such as water, saline solution, fixed oils, polyethylene glycols, glycerine, propylene glycol or other synthetic solvents. The preparation may contain one or more preservatives to prevent microorganism growth (e.g., antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose).

Pharmaceutical compositions for injection include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor ELT™ (BASF, Parsippany, N.J.) or phosphate buffered saline (PBS). The carrier can be a solvent or dispersion medium containing, for example, water, ethanol, polyol (e.g., glycerol, propylene glycol, and polyetheylene glycol), and suitable mixtures thereof. Antibacterial and antifungal agents include, for example, parabens, chlorobutanol, phenol, ascorbic acid and thimerosal. Including an agent that delays absorption, for example, aluminum monostearate and gelatin can prolong absorption of injectable compositions.

For transmucosal or transdermal administration, penetrants appropriate to the barrier to be permeated are used in the formulation. Such penetrants are known in the art, and include, for example, for transmucosal administration, detergents, bile salts, and fusidic acid derivatives; for transdermal administration, ointments, salves, gels, or creams. Transdermal delivery can also be achieved using patches.

Additional pharmaceutical formulations and delivery systems are known in the art and are applicable in the methods of the invention (see, e.g., *Remington: The Science and Practice of Pharmacy*, 20$^{th}$ ed., Lippincott, Williams & Wilkins (2000); Ansel et al., *Pharmaceutical Dosage Forms and Drug Delivery Systems*, 7$^{th}$ ed., Lippincott Williams & Wilkins Publishers (1999); Kibbe (ed.), *Handbook of Pharmaceutical Excipients American Pharmaceutical Association*, 3$^{rd}$ ed. (2000); *Pharmaceutical Principles of Solid Dosage Forms*, Technonic Publishing Co., Inc., Lancaster, Pa., (1993); and Poznansky et al., *Drug Delivery Systems*, R. L. Juliano, ed., Oxford, N.Y. (1980), pp. 253-315)

The methods of the invention include administering as a single or multiple dose each day (e.g., at a low dose), or intermittently (e.g., every other day, once a week, etc., optionally at a higher dose). Methods further include prohylactic delivery in order to reduce onset of a recall response.

Delivery routes or routes of administration include local, regional, and systemic in accordance with any protocol or route that achieves the desired effect. Administration can be achieved via inhalation (e.g., intra-tracheal), orally, intravenously, intraarterially, intravascularly, intrathecally, intraperitonealy, intramuscularly, subcutaneously, intracavity, transdermally (e.g., topical), transmucosally (e.g., buccal or nasal), by sustained release (e.g., gradual perfusion over time), as multiple doses or a single bolus. Local treatment methods also include oral or sublingual delivery.

A particular example is inhalation or intranasal administration, which provides bronchial or nasal delivery. The formulation can be administered in the form of an aerosol or mist. For aerosol administration, the formulation can be supplied in finely divided form along with a surfactant and propellant. The device for delivering the formulation to respiratory tissue can be in a formulation that vaporizes. Additional delivery systems known in the art include dry powder aerosols, liquid delivery systems, inhalers, air jet nebulizers and propellant systems (see, e.g., Patton (1998) Biotechniques 16:141; Sayani (1996) Crit. Rev. Ther. Drug Carrier Syst. 13:85; Dura Pharmaceuticals, San Diego, Calif.; Aradigm, Hayward, Calif.; Aerogen, Santa Clara, Calif.; and Inhale Therapeutic Systems, San Carlos, Calif.). The agent or compound that inhibits or reduces OX40 or OX40L signaling, expression or activity can therefore be formulated into an aerosol or non-aerosol.

Methods of identifying (screening) agents that reduce or inhibit OX40 or OX40L signaling, expression or activity are provided. In one embodiment, a method includes providing a test agent that reduces or inhibits signaling, expression or activity of OX40 or OX40 ligand (OX40L); and measuring a recall immune response in the presence of the test agent. In another embodiment, a method includes providing a test agent that binds to OX40 or OX40 ligand (OX40L); and measuring a recall immune response in the presence of the test agent. A reduction or inhibition of a recall response identifies the test agent as an agent that reduces or inhibits a recall immune response.

Methods of identifying (screening) agents that alleviate or ameliorate a symptom associated with a secondary or subsequent immune response to an antigen are also provided. In one embodiment, a method includes providing a test agent that reduces or inhibits signaling, expression or activity of OX40 or OX40 ligand (OX40L); and measuring a symptom associated with a secondary or subsequent immune response to an antigen in the presence of the test agent. In another embodiment, a method includes providing a test agent that binds to OX40 or OX40 ligand (OX40L); and measuring a symptom associated with a secondary or subsequent immune response to an antigen in the presence of the test agent. A reduction or inhibition of a symptom associated with a secondary or subsequent immune response to an antigen identifies the test agent as an agent that alleviates or ameliorates a symptom associated with a secondary or subsequent immune response to an antigen.

In one aspect of identifying (screening) an agent, the recall immune response is mediated at least in part by OX40/OX40L signaling. In additional aspects, the test agent includes an antibody (e.g., human or humanized), a modified OX40 or OX40L (e.g., sequence variant, subsequence, chimera or dominant negative form), an antisense nucleic acid molecule or RNAi that binds to OX40 or OX40L DNA or RNA, or a cytokine. Agents can be identified (screened) by detecting changes in a recall immune response or a symptom associated with a recall immune response in vivo (e.g., in a mammal). Exemplary symptoms are those set forth herein and known in the art and include, for example, swelling, enlargement, mucus production, rash, eosinophil infiltration, leukocyte or lymphocyte infiltration, cytokine or chemokine production, hyperplasia, inflammatory lesions or necrosis.

Methods of identifying (screening) agents that alleviate or ameliorate a symptom associated with asthma, for example, allergic asthma, are additionally provided. In one embodiment, a method includes providing a test agent that reduces or inhibits signaling, expression or activity of OX40 or OX40 ligand (OX40L); and measuring a symptom associated with asthma in the presence of the test agent. In another embodiment, a method includes providing a test agent that binds to OX40 or OX40 ligand (OX40L); and measuring a symptom associated with asthma in the presence of the test agent. A reduction or inhibition of a symptom associated with asthma identifies the test agent as an agent that alleviates or ameliorates a symptom associated with asthma.

Methods of identifying (screening) agents that alleviate or ameliorate a symptom associated with asthma, for example, allergic asthma, are further provided. In one embodiment, a method includes providing a test agent that reduces or inhibits signaling, expression or activity of OX40 or OX40 ligand (OX40L); and measuring asthma in the presence of the test agent. In another embodiment, a method includes providing a test agent that binds to OX40 or OX40 ligand (OX40L); and measuring asthma in the presence of the test agent. Alleviating or ameliorating asthma identifies the test agent as an agent for treating asthma.

In one aspect of identifying (screening) an agent, the asthma is mediated at least in part by OX40/OX40L signaling. In additional aspects, the test agent includes an antibody (e.g., human or humanized), a modified OX40 or OX40L (e.g., sequence variant, subsequence, chimera or dominant negative form), an antisense nucleic acid molecule or RNAi that binds to OX40 or OX40L DNA or RNA, or a cytokine.

Agents can be identified (screened) by detecting a change in an undesirable or adverse symptom or complication associated with asthma in vivo (e.g., in a mammal). Exemplary symptoms are those set forth herein and known in the art and include, for example, swelling, enlargement, mucus production, eosinophil infiltration (e.g., of lung), leukocyte or lymphocyte infiltration (e.g., of lung), cytokine or chemokine production (e.g., Th2 cytokine production), hyperplasia (e.g., of goblet cell or mucus secreting epithelium), inflammatory lesions or necrosis (e.g., of lung), wheezing, shortness of breath, chest tightness, cough, and sputum production, airflow restriction, airway edema or mucus production.

Kits that include one or more agents that reduce or inhibit or prevent OX40 or OX40L signaling, expression or activity, packaged into suitable packaging material, are also provided. A kit typically includes a label or packaging insert including a description of the components or instructions for use in vitro, in vivo, or ex vivo, of the components therein. A kit can contain a collection of such components.

In one embodiment, a kit includes an agent sufficient to reduce or inhibit or prevent OX40 or OX40L signaling, expression or activity and instructions for treating a recall immune response. In another embodiment, the container includes two or more such agents. In yet another embodiment, the kit or container includes an immune-response inhibiting or immune-response reducing agent.

The term "packaging material" refers to a physical structure housing the components of the kit. The packaging material can maintain the components sterilely, and can be made of material commonly used for such purposes (e.g., paper, corrugated fiber, glass, plastic, foil, ampules, etc.). The label or packaging insert can include appropriate written instructions.

Kits of the invention therefore can additionally include labels or instructions for using the kit components in a method of the invention. Instructions can include instructions for practicing any of the methods of the invention described herein including treatment methods. Thus, for example, a kit can include one or more agents that inhibit or reduce or prevent OX40 or OX40L signaling, expression or activity, together with instructions for administering to a subject in a treatment method of the invention.

The kit components (e.g., agents) can be packaged in unit dosage form for ease of administration and uniformity of dosage. "Unit dosage form" refers to physically discrete unitary dosages for administration to the subject to be treated; each unit contains a predetermined quantity of compound that produces a desired effect, optionally in combination with a pharmaceutical carrier or excipient.

The instructions may be on "printed matter," e.g., on paper or cardboard within or affixed to the kit, or on a label affixed to the kit or packaging material, or attached to a vial or tube containing a component of the kit. Instructions may additionally be included on a computer readable medium, such as a disk (floppy diskette or hard disk), optical CD such as CD- or DVD-ROM/RAM, magnetic tape, electrical storage media such as RAM and ROM and hybrids of these such as magnetic/optical storage media.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described herein.

All publications, patents and other references cited herein are incorporated by reference in their entirety. In case of conflict, the specification, including definitions, controls.

As used herein, the forms "a", "and," and singular "the" include plural referents unless the context clearly indicates otherwise. Thus, for example, reference to an "agent" or an "antibody" includes a plurality of agents and antibodies, and reference to "a symptom" includes reference to one or more symptoms.

A number of embodiments of the invention have been described. Nevertheless, it will be understood that various modifications may be made without departing from the spirit and scope of the invention. Accordingly, the following examples are intended to illustrate but not limit the scope of invention described in the claims.

EXAMPLES

Example 1

This example describes various materials and methods.

Mice

The studies conform to the principles outlined by the animal Welfare Act and the National Institutes of Health guidelines for the care and use of animals in biomedical research. Female C57BL/6 mice (6-8 week old) were purchased from Jackson Labs (Bar Harbor, Me.). OT-II TCR transgenic mice (Barnden et al., Immunol Cell Biol. (1998) 76:34), were used as a source of Vβ5/Vα2 CD4+ T cells responsive to peptide 323-339 of ovalbumin (OVA). OX40-deficient OT-II TCR transgenic mice were generated by crossing OT-II mice with OX40−/− mice.

Induction of Allergic Airway Inflammation

The protocol for induction of pulmonary inflammation via antigen sensitization and aerosol challenge was as described previously (Jember et al., J Exp Med. (2001) 193:387). Briefly, groups of 4 C57BL/6 mice were sensitized by intraperitoneal (i.p.) injection of 20 μg OVA protein (chicken egg albumin; Sigma-Aldrich), adsorbed to 2 mg aluminum hydroxide (Alum; Pierce) in phosphate buffered saline (PBS) on day 0. Unsensitized (naïve) mice received 2 mg Alum in PBS. On day 25 or later, mice were challenged via the airways with OVA (5 mg/ml in 15 ml of PBS) for 30 min, once a day for four consecutive days, by ultrasonic nebulization (Jember et al., (2001), supra). To block OX40-OX40L interaction, mice were injected i.p. with 200 μg of rat anti-mouse-OX40L blocking mAb (RM134L, rat IgG2bκ; Akiba et al., J Immunol. (1999) 162:7058) or isotype control antibody (IgG2b); given on the indicated days in PBS, 30 min prior to OVA challenge.

Analysis of the Asthma Phenotype

Airway responsiveness (AHR) was measured in vivo 1-3 hr after the last aerosolized OVA exposure by recording respiratory curves by whole-body plethysmography (Buxco Technologies) in response to inhaled methacholine (MCh; 1.25-10 mg/ml; Aldrich chemical) as described (Jember et al., (2001), supra). Bronchoalveolar lavage (BAL) cytology, lung histopathology, OVA-specific and total IgE and lung cytokine profiles obtained by ELISA were determined as described (Jember et al., (2001), supra). All data unless otherwise indicated were collected 24 h after the final antigen challenge.

Stimulation of Lung, Peribronchial Lymph Node, and Spleen Cells In Vitro

Peribronchial lymph nodes (PBLNs) and spleens were collected at the time of lung harvest. Lavaged lungs were digested with Hanks' balanced salt solution (HBSS; Gibco) supplemented with 3 mg/ml collagenase (Type V; Boehringer Mannheim), 0.1 mg/ml Dnase (Sigma), 100 μg/ml streptomycin (Invitrogen), and 100 U/ml penicillin (Invitrogen) for 60 min at 37° C. After lysing red blood cells (RBCs) with ACK lysis buffer, PBLN, spleen and lung cells were resuspended in RPMI-1640 medium (Gibco) supplemented with 10% FCS (Omega Scientific), 1% L-glutamine (Invitrogen), 100 μg/ml streptomycin, 100 U/ml penicillin and 50 μM 2-mercaptoethanol (Sigma). Splenocytes ($2\times10^5$ cells/well), lung cells ($8\times10^5$ cells/well), or PBLNs cells ($2\times10^5$ cells/well) were plated in round-bottomed 96-well microtiter plates in 200 μl with increasing concentrations of OVA (10-100 μg/ml) for 72 hrs at 37° C. After 56 hr, 1 μCi of $3^H$-thymidine (ICN Biomedicals) was added to each well. The cells were harvested 16 hr later, and thymidine incorporation measured using a Betaplate scintillation counter. Each in vitro stimulation was performed in quadruplicate. Supernatants were harvested after 40 hr for cytokine analysis.

Generation and Adoptive Transfer of Ova-Specific Th2 Cells

Lymph node and spleen cells from wild-type (OX40+/+) OT-II mice or OT-II OX40-deficient (OX40−/−) mice were pooled and CD4 cells isolated as previously described (Gramaglia et al., J Immunol. (1998) 161:6510). The purity of CD4+ T cells was confirmed to be >98% by FACS analysis. To generate memory Th2 cells, naïve T cells ($1\times10^6$ cells/ml) were cultured in two ways: with plate-bound αCD3 (3 μg/ml) and soluble αCD28 (10 μg/ml), or with $2\times10^6$/ml syngeneic splenic APCs and 0.1 μM OVA peptide, plus IL-2 (5 ng/ml), IL-4 (20 ng/ml), αIFN-γ (10 μg/ml), and αIL-12 (10 μg/ml), for 3 days at 37° C. At the end of this culture, cells were removed, washed, and then cultured for another 3-6 d without further stimulation.

In some cases, primed T cells were labeled with CFSE (5- and 6-carboxyfluorescein diacetate succinimidly ester C-1157; Molecular Probes, Eugene, Oreg.) and $2\times10^6$ were injected into the tail vein of naïve C57BL/6 mice in 200 μl. One day after transfer of cells, mice were challenged with inhaled OVA (5 mg/ml in 15 ml PBS) for 30 min daily for 2 consecutive days. Animals were sacrificed for analyses 1 day later. Control mice received inhaled PBS only. In vivo cell division and T cell accumulation were assessed by tracking transferred T cells with flow cytometry based on co-expression of CFSE and Vα2.

Following the primary culture, an aliquot of primed T cells were retained to determine proliferation, survival, and cytokine production in recall responses in vitro. $5\times10^5$ CD4 T cells/ml were recultured with $2\times10^6$/ml syngeneic splenic APCs and OVA peptide. IL-4, IL-5, IL-13, and IFN-γ levels from cell supernatants were determined by ELISA at 40 hr. Proliferation was measured in triplicate by the incorporation of $^3$H-thymidine (1 μCi/well; ICN Pharmaceuticals) during the last 12 hr of culture. T cell survival was determined by trypan blue exclusion.

Flow Cytometry Analysis

Cells were stained with FITC-conjugated anti-CD4, PE-conjugated anti-OX40, Cychrome-conjugated anti-CD44, or PE-conjugated anti-Vα2 at 4° C. for 30 min. Immunostained cells were analyzed on a FACScan flow cytometer (Becton Dickenson) using CELLQest software.

Example 2

This example describes data indicating that OX40 is expressed on memory Th2 cells.

To determine if memory CD4 cells express OX40, C57BL/6 mice were immunized i.p. with OVA adsorbed to alum (FIG. 1A. and 1B, primed). Twenty-five days later mice were challenged by inhalation of nebulized OVA on 4 consecutive days (FIG. 1A. and 1B, primed/challenged). T cells from mice primed 4 weeks prior with OVA in alum were stained.

A significant number of CD44hi memory CD4 cells in lymph nodes that expressed OX40 at low/moderate levels were visualized. In contrast, CD44lo naïve CD4 cells did not express OX40 without antigen exposure (FIG. 1A), shown previously (Gramaglia et al., (1998) J Immunol. 161:6510). Unimmunized mice also contained a proportion of CD44hi CD4 cells that expressed OX40 at low levels suggesting that OX40 can be readily available to some memory T cells. OX40 levels were upregulated on responding CD44hi memory T cells in lung draining lymph nodes after challenge with aerosolized antigen (FIG. 1A); the absolute number of OX40 positive CD44hi CD4 cells (mean of 4 mice) increased markedly (FIG. 1C, and see below).

This large increase in OX40-expressing CD44hi cells was not observed in unprimed mice challenged with aerosolized antigen. Thus, these results directly indicate a memory T cell response and accumulation of memory effector cells.

Few CD4 cells were present in the lungs of primed but unchallenged mice, and OX40 was not detected on either CD44hi or lo cells (FIG. 1B). However, after antigen challenge a large number of OX40-expressing CD4/CD44hi cells were present in the lung (FIG. 1B).

These data indicate that OX40 is expressed on memory/memory effector T cells and is available to play a role in the secondary response that occurs after re-encounter with antigen.

Example 3

This example describes data indicating that preventing OX40/OX40L interaction impairs development of airway hyperreactivity and eosinophilia.

Figure 2:
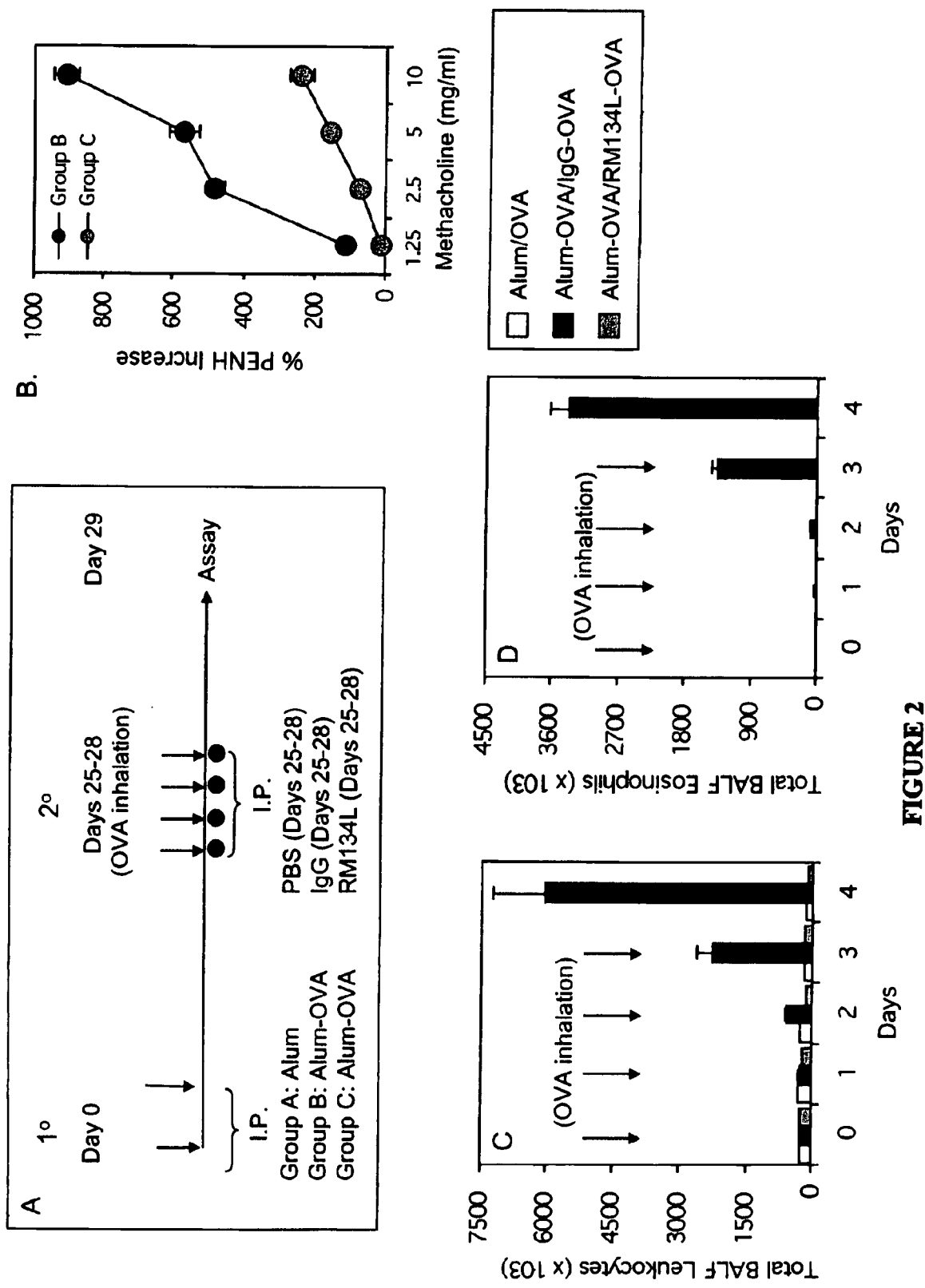
FIGS. 2A-2D show that anti-OX40L suppresses memory T cell induced AHR and airway inflammation. (A) Protocol for anti-OX40L administration. Unprimed control mice injected with alum alone (Alum), primed mice sensitized with OVA adsorbed to alum (Alum-OVA). Mice were challenged on 4 consecutive days (days 25-28; indicated by arrows) with either PBS (Group A: Alum/OVA), control IgG (Group B: Alum-OVA/IgG-OVA) or anti-OX40L (Group C: Alum-OVA/RM134L-OVA). (B) mice airway hyperreactivity (AHR). Results are the mean percent change in Penh levels above baseline, after increasing methacholine concentrations. Values are calculated from four mice in each group per study (similar results were observed in 3 studies). (C) Total leukocyte numbers in bronchoalveolar lavages (BAL) at different times (0, 1, 2, 3, and 4 days) after OVA challenge (indicated by arrows). (D) Total eosinophil numbers from differential stained BAL cytospins. Results are the mean number of cells±SEM from two separate studies (four mice per group in each study).

Characteristic features of allergic asthma are produced in mice sensitized with OVA that are subsequently challenged later by OVA inhalation (Wills-Karp, M. Annu Rev Immunol. (1999) 17:255, Jember et al., (2001), supra). To examine the contribution of OX40/OX40L interactions to lung inflammation, a blocking anti-OX40L mAb was administered to OVA-sensitized mice at the time of re-challenge with aerosolized antigen (FIG. 2A). In brief, unprimed control mice were injected i.p. with alum alone, while primed mice were sensitized with OVA adsorbed to alum. Twenty-five days later, all mice were challenged with aerosolized OVA on 4 consecutive days (days 25-28). Either PBS (Group A: Alum/OVA), or control IgG (Group B: Alum-OVA/IgG-OVA) or anti-OX40L (Group C: Alum-OVA/RM134L-OVA) were administered i.p. on each challenge day. 1-3 hr after the last challenge, individual mice were assessed for AHR.

OVA-immunized mice treated with isotype control antibody developed AHR. In contrast, administration of anti-OX40L dramatically reduced the degree of AHR (FIG. 2B). Sensitized mice treated with control Ab during aerosol challenge (Alum-OVA/IgG-OVA) responded with an increase in the total number of cells in BAL (FIG. 2C), which was evident as early as 48 hrs and was mostly eosinophils (FIG. 2D). In striking contrast, administration of anti-OX40L during the challenge period (Alum-OVA/RM134L-OVA) virtually eliminated the increase in total leukocytes (FIG. 2C) and eosinophils (FIG. 2D).

No cell infiltration was seen in unprimed but challenged animals. Thus, these results directly demonstrate that OX40/OX40L interactions mediate recall response.

Example 4

This example describes data indicating that blocking OX40/OX40L interactions inhibits development of airway tissue eosinophilia, goblet-cell hyperplasia, and mucus production.

To confirm the findings from lung lavages, lung sections were histologically evaluated. In brief, groups of mice were immunized and challenged as described in Example 3. 24 hr after the final OVA aerosol challenge, lung tissue was stained with H&E (×100) for quantitation of inflammatory infiltrates (FIG. 3A) and periodic acid-Schiff (PAS, ×200; purple-red staining) to highlight the mucus-secreting cells (FIG. 3B), in sensitized and challenged animals receiving control Ig or anti-OX40L. Sections were graded for inflammation severity (FIG. 3A) and mucus production (FIG. 3B).

Figure 3:
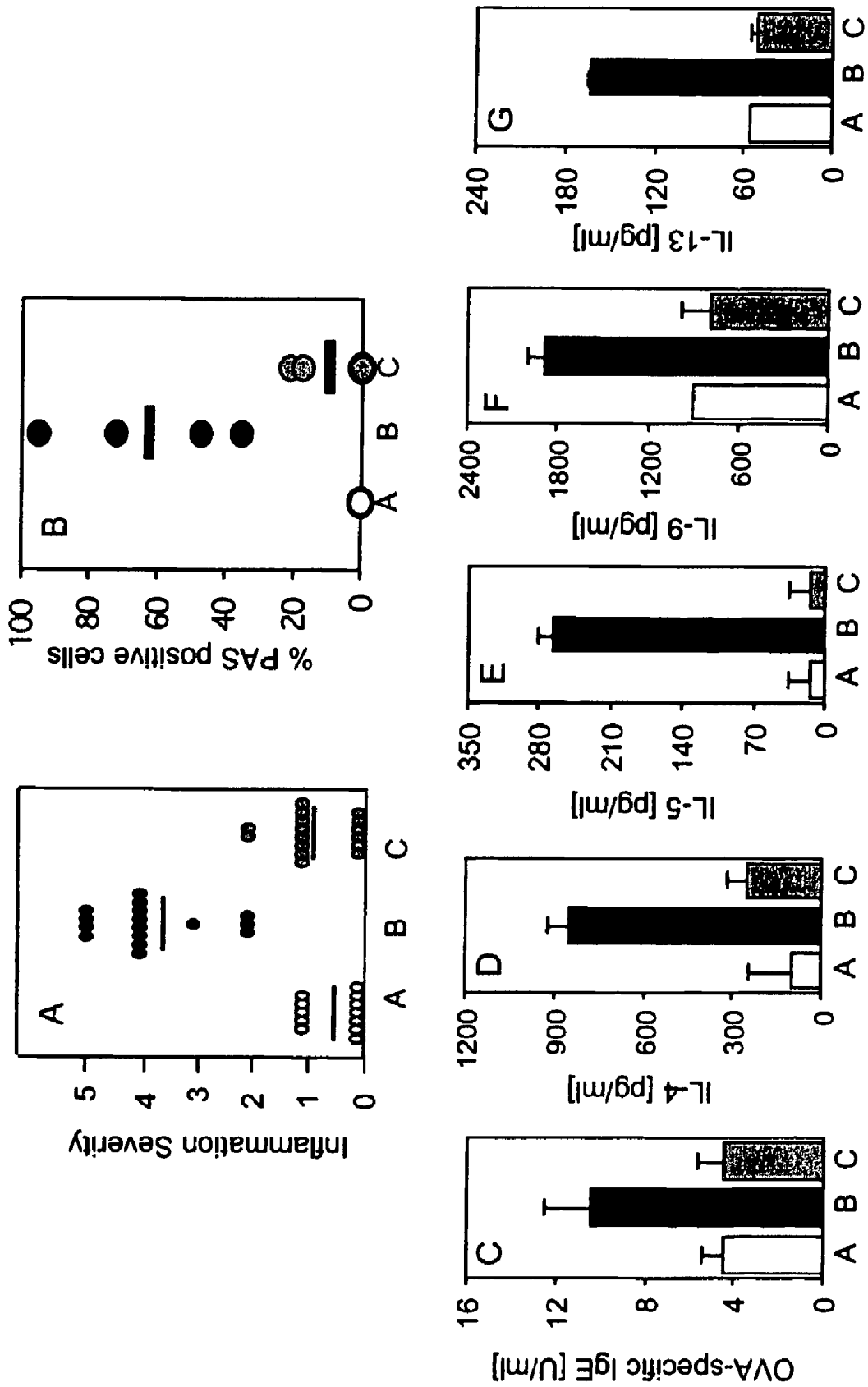
FIGS. 3A-3G show that anti-OX40L inhibits lung infiltration, goblet cell hyperplasia, mucus, serum IgE and BAL Th2 cytokine production. (A) inflammation severity and (B) mucus production with groups A (□), B (■), and C (☒) corresponding to the groups in FIG. 2. Results are the mean score±SEM from four separate studies (four mice per group in each study). Sera analyzed for (C) OVA-specific IgE, and BAL analyzed for (D) IL-4, (E) IL-5, (F) IL-9, and (G) IL-13. Results are the mean values±SEM from two separate studies (four mice per group in each study).

Mice receiving control antibody developed inflammatory lesions, characterized by a predominance of eosinophils and lymphocytes, and hyperplasia of mucus-secreting bronchial epithelial cells (FIG. 3A). In contrast, lungs from anti-OX40L treated animals exhibited almost normal bronchial epithelium, and few infiltrating cells around the bronchioles and blood vessels. Although many PAS$^+$ (mucus-secreting) cells were detected in the airway of mice sensitized and challenged that received the control Ab, treatment with anti-OX40L markedly reduced the number of PAS$^+$ cells (FIG. 3B).

These results indicate that blocking OX40/OX40L interactions inhibits development of airway tissue eosinophilia, goblet cell hyperplasia, and mucus production.

Example 5

This example describes data indicating that allergen-induced IgE and Th2 cytokine production are reduced in anti-OX40L treated mice.

As an indirect test of whether OX40 signals were controlling memory Th2 response contributing to the asthmatic reaction, IL-4, IL-5, IL-9 and IL-13 cytokine levels in the BAL, and production of the Th2-associated antibody IgE, were measured in serum 24 hr after the final OVA aerosol challenge (Example 4).

Treatment with anti-OX40L prevented the increase in IgE resulting from the recall response (FIG. 3C) as well as all Th2 cytokines (FIGS. 3D-G) associated with the recall response. IFN-γ was absent or present at low levels in all groups, indicating that there was not a switch to a Th1 response.

Example 6

This example describes data indicating that OX40 signals modulate memory effector T cell accumulation in secondary lymphoid organs.

To determine whether functional antigen-reactive T cells were present in mice in which OX40 signals were blocked, OVA-specific proliferation (at 72 hr with 10 µg/ml OVA), and production of Th2 cytokines (IL-5; similar results were obtained for IL-13) was measured in vitro. In brief, mice were immunized and challenged as described in Example 3. One day after the last OVA challenge, lung and lymph node cells were cultured in medium alone or in the presence of increasing doses of OVA (10, 50, 100 µg/ml). (Group A: Alum/OVA; Group B: Alum-OVA/IgG-OVA; Group C: Alum-OVA/RM134L-OVA).

Robust responses were detected in lung cell cultures from OVA-primed and challenged mice but not in unprimed challenged mice (FIGS. 4A and 4B, compare grp B and grp A). These results further indicate the memory effector response and that a functional primary response did not result from exposure to airborne antigen alone. Animals treated with anti-OX40L during the recall response showed little or no OVA-specific T-cell reactivity in the lungs (FIGS. 4A and 4B, grp C).

To determine whether recall responses were absent at other sites, spleen and lung draining lymph nodes were examined. OVA-reactivity was significantly reduced in secondary lymphoid organs after anti-OX40L treatment (FIGS. 4C and 4D). These results indicate that the effect of OX40/OX40L blockade is not tissue specific but, rather, that OX40 signaling is critical for development of functional memory effector cells after memory T cells re-encounter antigen.

OX40 is only present on antigen-responding or antigen-experienced T cells. The accumulation of OX40-expressing CD4 cells was measured over time. In brief, peribronchial lymph node, lung, and BAL cells from unimmunized and challenged mice, or OVA-immunized and challenged mice treated with control Ab vs. anti-OX40L Ab, were harvested before (day 0) or on the indicated days after the first OVA challenge. T cells were stained for CD4 and OX40. Total numbers of OX40+ CD4 T cells were calculated from four mice in each group after gating on viable CD4+ T cells.

Figure 4:
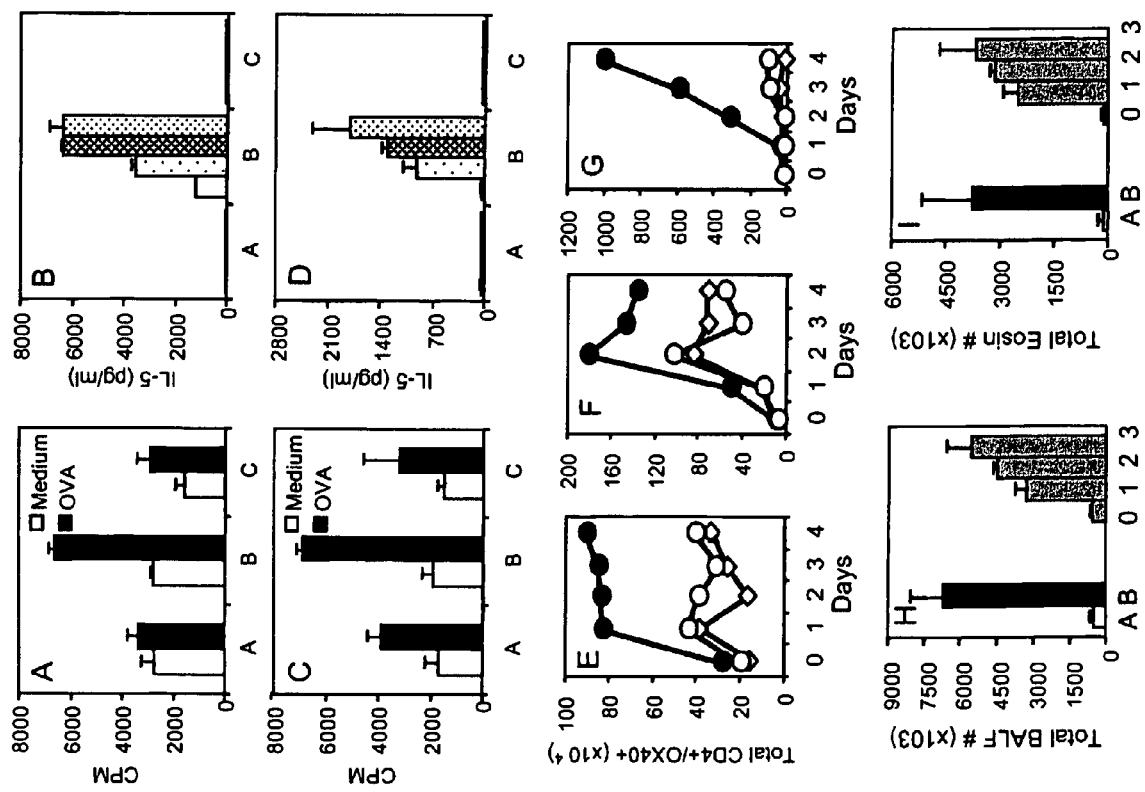
FIGS. 4A-4I show that OX40 signals control memory T cell responses in secondary lymphoid organs. (A, B) Lung and (C, D) lymph node cells were assayed for proliferation (A, C) in the presence and absence of OVA (10 µg/ml), (B, D) or IL-5 production to increasing concentrations of OVA (0, 10, 50 or 100 µg/ml, left to right). (Group A: Alum/OVA; Group B: Alum-OVA/IgG-OVA; Group C: Alum-OVA/RM134L-OVA). Results are the mean±SEM from quadruplicate cultures and are representative of three studies. Peribronchial lymph node (E), lung (F), and BAL (G) cells from unimmunized and challenged mice (♦), or OVA-immunized and challenged mice treated with control Ab (●) vs. anti-OX40L Ab (○). T cells were stained for CD4 and OX40 and total numbers of OX40+ CD4 T cells were calculated. Similar results were observed in 3 studies. (H) Total leukocyte and (I) eosinophil numbers in BAL from mice given anti-OX40L throughout challenge (day 0), or 1, 2, or 3 days after the initial challenge. Results are the mean±SEM from one study with four mice per group.

As shown in FIG. 4 (see, also, FIG. 1), before antigen challenge only a low number of T cells expressed OX40. In contrast, after OVA challenge, a large increase was observed in the number of CD4$^+$OX40$^+$ cells in the bronchial lymph node (FIG. 4E), lung (FIG. 4F), and BAL (FIG. 4G) in primed and challenged mice. The increase was far greater than in unprimed challenged mice, reflecting the responding memory effector T cell population. The number of OX40$^+$ cells in the LN peaked at day 1, whereas the number in the BAL rose progressively from day 2 over the 4-day aerosol exposure. These results suggest that the initial memory T cell response developed in the secondary lymphoid organs, and within 24 hr the T cells migrated to the lung, which correlates with other published data (Kaminuma et al., Eur J Immunol. (2001) 31:2669). Significantly, treatment of mice with anti-OX40L reduced the number of CD4$^{+OX}$40$^+$ cells visualized in the lymph node at the peak of response at day 1, and subsequently. Consequently, few activated OX40$^+$T cells were then observed in the lung and BAL.

These results suggest that OX40/OX40L interactions early in the response of a memory T cell control their ability to expand in numbers and survive thereby forming a large population of memory effector T cells.

As further evidence of the role of OX40/OX40L interactions, kinetic blocking studies where mice received anti-OX40L 1, 2, or 3 days after the initial aerosol were performed (FIGS. 4H and 4I). Although delaying anti-OX40L treatment by 1 or 2 days reduced the response by 50% and 30%, the most dramatic effect was seen when OX40/OX40L interactions were inhibited at the time of initial encounter with recall antigen.

Example 7

This example describes data indicating that OX40-deficient OVA-specific Th2 cells do not survive efficiently in recall responses.

To further investigate the role of OX40 in recall responses of antigen-primed Th2 cells, OVA-specific OX40-deficient CD4 cells were produced by crossing OX40-knockout mice to OT-II TCR transgenic mice. Naïve CD4 cells from wild-type (OX40+/+) or OX40-deficient (OX40−/−) OT-II mice were cultured in vitro with peptide and APCs under Th2 (IL-4, anti-IL-12, and anti-IFN-γ) polarizing conditions for a time period that allows primary T cell expansion and contraction to proceed normally. Proliferation and survival were measured over 6 days and cytokine production (IL-4 and IL-5) measured at 40 hr. Other investigators have reported that such in vitro stimulated cells mimic in vivo generated memory cells (Hu et al., Nat. Immunol. (2001) 2:705, Harbertson et al., J. Immunol. (2002) 168:1095) and can also be used in adoptive transfer experiments to directly induce lung inflammation (Cohn et al., J Exp Med. (1997) 186:1737, Hansen et al., J Clin Invest. (1999) 103:175).

Figure 5:
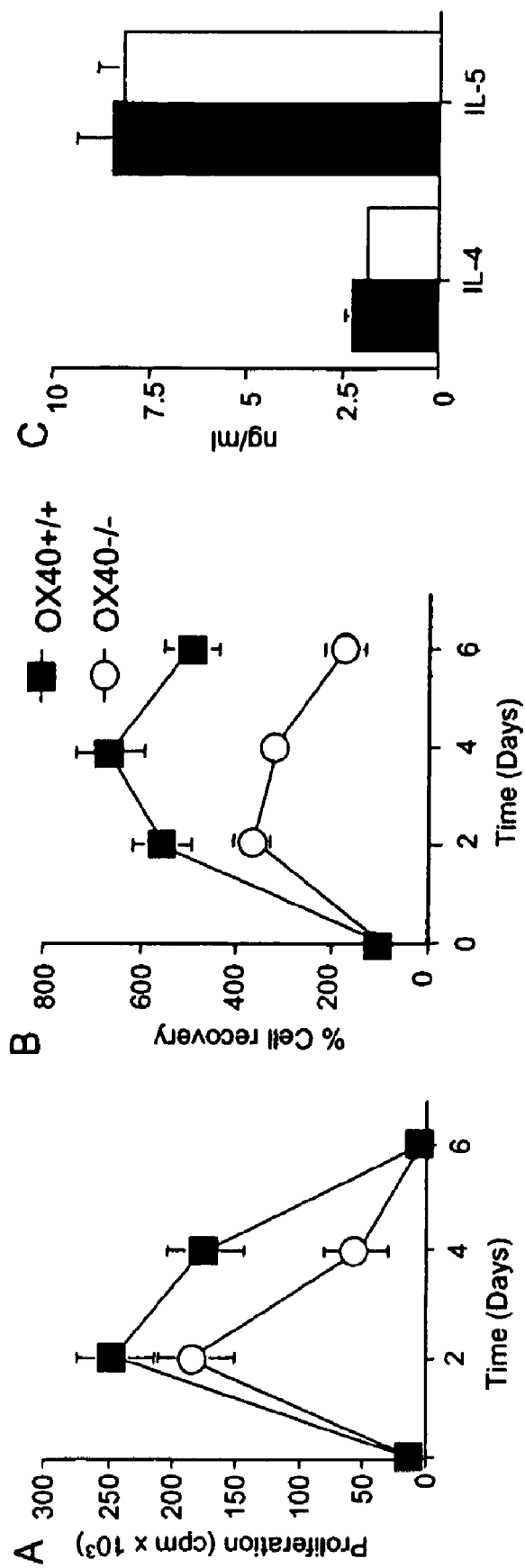
FIGS. 5A-5C show that primed OX40−/− T cells do not survive efficiently in recall responses in vitro. OVA-specific Th2 memory cells were generated in vitro as described in Example 7. (A) Proliferation, (B) survival and (C) IL-4/IL-5 production of primed T cells re-stimulated with OVA and APCs. Data are means±SEM from triplicate cultures, and representative of 2 separate studies.

Re-stimulation of primed OX40+/+Th2 cells in vitro with OX40L-sufficient APCs resulted in proliferation, expansion, survival, and production of Th2 cytokines (FIG. 5). Primed OX40−/− T cells secreted Th2 cytokines normally indicating that there is no apparent role for OX40 in this T cell activity, and OX40−/− T cells also initially proliferated comparably with wt T cells. However, far fewer T cells survived in the secondary response in the absence of OX40 signals, which was also indicated by weak proliferation late in culture (FIGS. 5A and B). Similar results were obtained if naïve T cells were stimulated with antigen or anti-CD3 in primary cultures.

Figure 6:
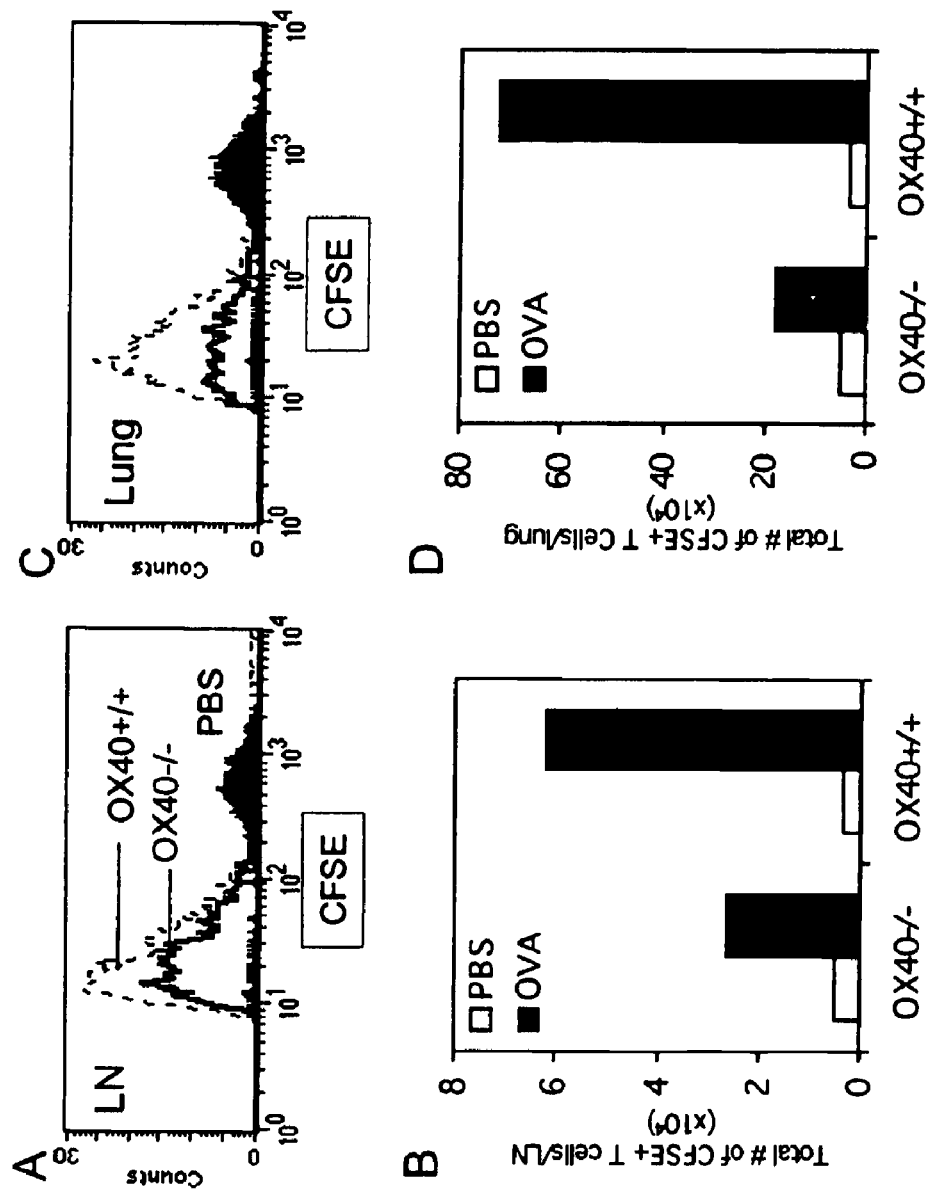

To determine if a similar requirement for OX40 was apparent in vivo during a recall response to aerosolized antigen, in vitro primed T cells were labeled with CFSE, adoptively transferred into naïve mice recipients, and then the mice were challenged intranasally with OVA (FIG. 6). In brief, OVA-specific Th2 memory cells were generated in vitro as described above, from wild type (OX40+/+) or OX40-deficient (OX40−/−) OT-II TCR transgenic mice. Primed T cells were labeled with CFSE and injected i.v. into naïve C57BL/6 mice. Recipient mice were subsequently exposed to inhaled OVA or PBS on two consecutive days. 1 day after the last OVA challenge, peribronchial lymph node and lung were analyzed by flow cytometry for division and accumulation of transferred CFSE/Vα2 positive CD4 T cells.

Challenge with PBS did not result in division (FIGS. 6A and C) or expansion (FIGS. 6B and D) of either OX40+/+ or OX40−/− T cells in draining lymph nodes or lung. Challenge with OVA resulted in pronounced division of all OX40+/+T cells. Accumulation in numbers was observed in lymph nodes and was particularly evident in lung. Correlating with the in vitro data, recovered OX40−/− T cells displayed the same division profile as their wt counterparts (FIGS. 6A and C), but in total approximately 4-fold fewer accumulated at the end of the antigen challenge period (FIGS. 6B and D).

These results directly mimic the data obtained by tracking OX40-expressing T cells after OX40L blockade (FIGS. 4E-G). Thus, OX40 signals regulate the number of memory effector T cells generated after memory T cells re-encounter antigen.

Example 8

This example describes data indicating that primed OX40-deficient OVA-specific Th2 cells do not efficiently promote lung inflammation.

Figure 7:
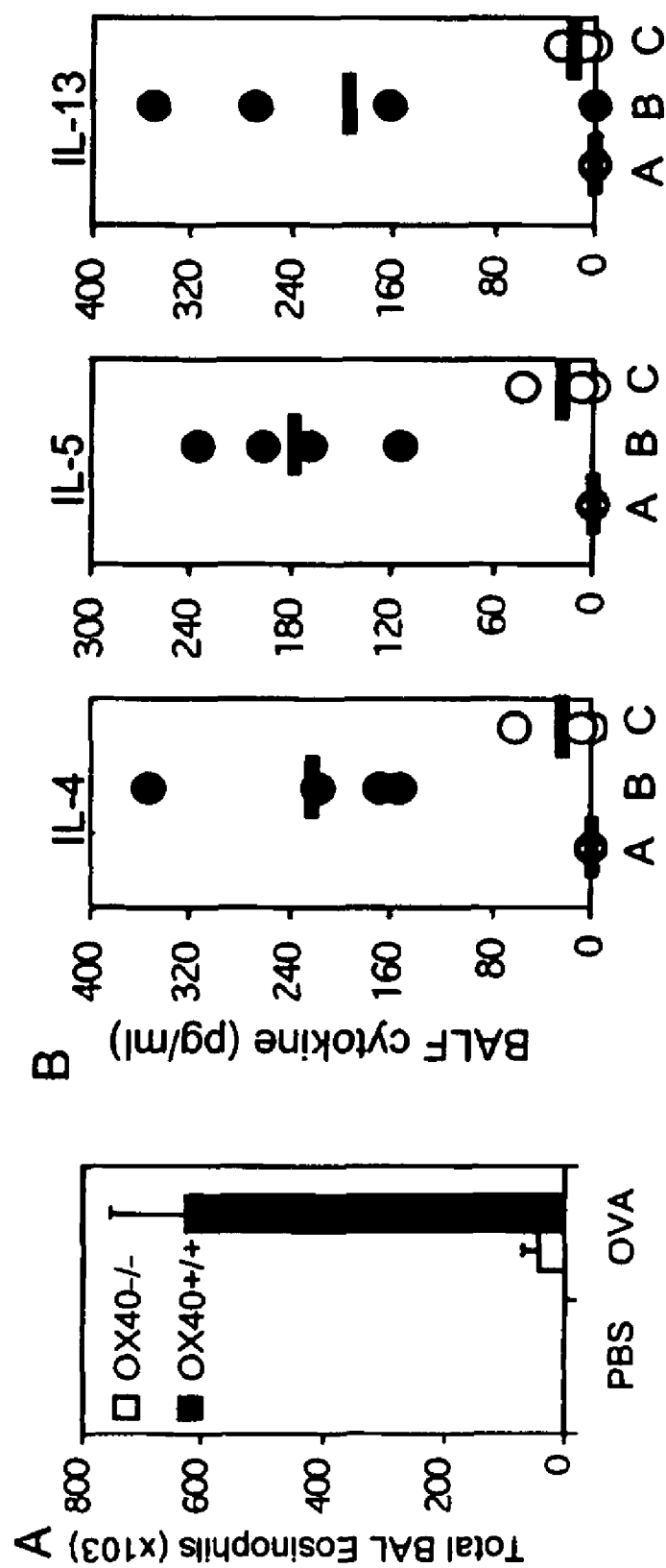

To correlate lack of expansion/survival of memory effector cells with reduced lung inflammation, eosinophilia, lung histology and Th2 cytokines were analyzed following adoptive transfer of primed OX40−/− OT-II Th2 cells (FIG. 7). In brief, OVA-specific Th2 memory cells were generated in vitro as described in Example 7, from wild type (OX40+/+) or OX40-deficient (OX40−/−) OT-II TCR transgenic mice. Primed T cells were injected i.v. into naïve C57BL/6 mice. Recipient mice were subsequently exposed to aerosolized OVA or PBS on two consecutive days. Eosinophil numbers in BAL determined 24 hr after the last OVA challenge. IL-4, IL-5, and IL-13 levels in BAL were determined from mice with wt T cells challenged with PBS, wt T cells challenged with OVA, or OX40−/− T cells challenged with OVA Transfer of wild-type cells followed by repeated intranasal OVA challenge induced profound inflammation accompanied by production of Th2 cytokines in BAL (FIG. 7A, 7B). In contrast, mice receiving OX40-deficient cells exhibited only a small increase in total numbers of eosinophils recovered from the BAL (FIG. 7A), a relatively normal lung histology and reduced Th2 cytokines (FIG. 7B).

These results indicate that OX40 expressed on memory Th2 cell is required for lung inflammation.

Example 9

This example describes data indicating that OX40/OX40L interactions control late secondary and tertiary recall responses to inhaled antigen.

Figure 8:
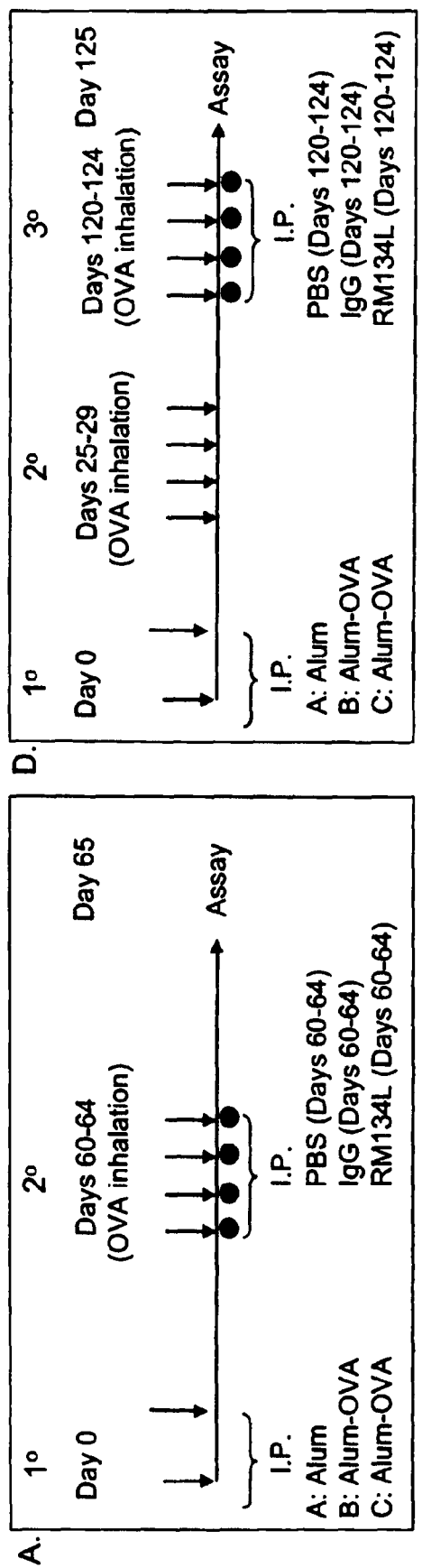
Figure 8:
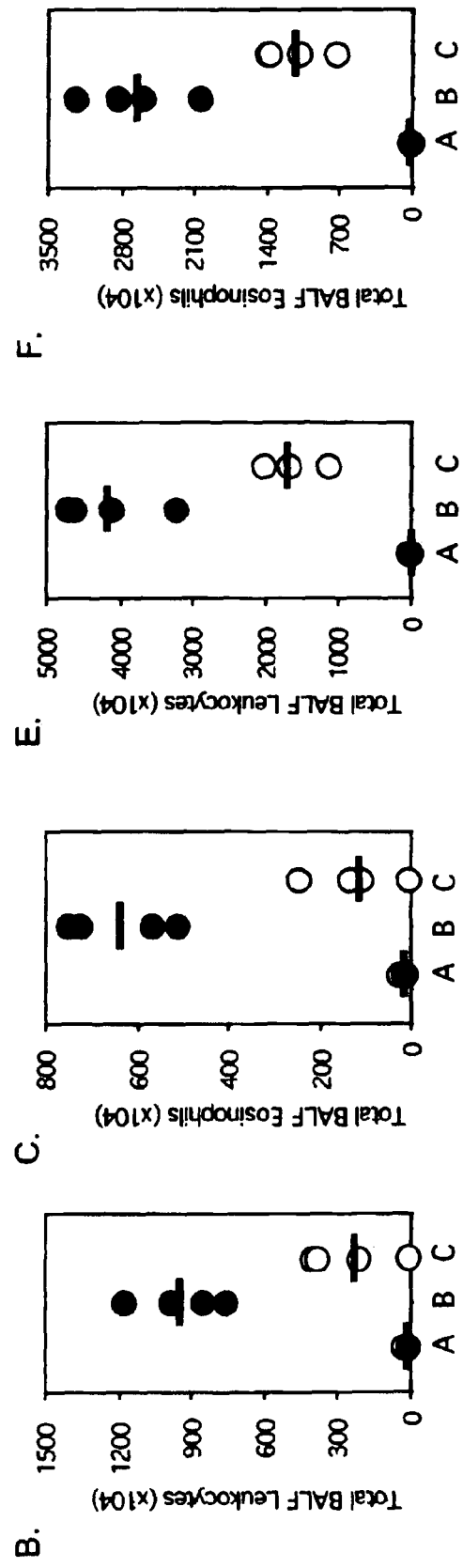

To determine whether OX40/OX40L interactions are also critical for the response of memory T cells that persist for longer periods of time and survive following a secondary response, mice were primed for 8 weeks and anti-OX40L administered during the secondary response to aerosolized antigen (FIG. 8A). Protocol A: In brief, unprimed control mice were injected i.p. with alum alone, while primed mice were sensitized with OVA adsorbed to alum. Sixty days later, all mice were challenged with aerosolized OVA on 4 consecutive days (days 60-64). Either PBS (Group A: Alum/OVA), or control IgG (Group B: Alum-OVA/IgG-OVA) or anti-OX40L (Group C: Alum-OVA/RM134L-OVA) were administered i.p. on each challenge day.

One day after the last challenge mice were sacrificed and airway eosinophilia and Th2 cytokine production determined. Total leukocyte and eosinophil numbers were enumerated in BAL from mice in protocol A and protocol B (below) respectively. Analysis of Th2 cytokines showed the same profile as cell infiltration.

As before, blocking OX40 signaling strongly inhibited all aspects of lung inflammation, including total leukocyte (FIG. 8B) and eosinophil (FIG. 8C) infiltration, and production of Th2 cytokines.

In additional studies, mice were primed for 4 weeks, challenged with aerosolized antigen in a secondary response without blocking OX40L, rested for 13 weeks, and then challenged again but with anti-OX40L blockade (FIG. 8D). Protocol B: In brief, unprimed control mice were injected i.p. with alum alone, while primed mice were sensitized with OVA adsorbed to alum. On days 25-29 all mice were challenged in a secondary response with aerosolized OVA. Ninety-one days later (day 120), all mice were challenged in a tertiary response with aerosolized OVA on 4 consecutive days (days 120-124). Either PBS (Group A: Alum/OVA), or control IgG (Group B: Alum-OVA/IgG-OVA) or anti-OX40L (Group C: Alum-OVA/RM134L-OVA) were administered i.p. on each challenge day.

Inhibiting OX40 signals during this tertiary response again strongly inhibited lung inflammation (FIGS. 8E and F), with a greater than 50% reduction in cellular infiltration. As no lung inflammation was observed in unsensitized control mice repeatedly exposed to aerosolized antigen, ruling out any primary response (FIGS. 8E and F, grp A), these data demonstrate that blocking OX40/OX40L interactions severely limits recall response of memory Th2 populations, including responses that can persist for extended periods of time (e.g., tertiary recall responses).

Example 10

This example describes conclusions that can be drawn from the in vivo studies employing the animal model described herein.

The data herein indicate that OX40-OX40L interactions contribute to antigen-specific memory that mediates allergic lung inflammation. Exposure of previously sensitized animals to antigen via the airways is accompanied by large increases in the number of OX40-expressing memory/memory effector Th2 cells, both in lungs and in secondary lymphoid organs. This effector Th2 response was associated with eosinophilia and the development of airway hyper-responsiveness. In vivo studies therefore indicate that preventing OX40-OX40L interactions during the memory response inhibited the Th2 response and the associated asthmatic symptoms. Modulating peripheral acute phase inflammatory responses can therefore be achieved by modulating OX40-OX40L interactions.

Analysis of BAL and dispersed lung showed that an OX40/OX40L signaling inhibitor, antibody against OX40L, reduced absolute numbers of activated (OX40$^+$) memory effector T cells, consistent with OX40 involvement in memory T cell recruitment. However, reduced numbers of activated OX40$^+$T cells were also observed in secondary lymphoid organs, along with reduced antigen-specific activity, indicating that preventing OX40/OX40L interactions did not simply block T cells from entering the lung. Other studies of lung inflammation have suggested that memory T cells do not proliferate in the lung in response to intranasal antigen challenge, but proliferate in the lymph nodes (Harris et al., J Exp Med. (2002) 195:317). Moreover, prior reports show that T cell emergence in the lung is only appreciable 24-48 hr after antigen re-exposure (Kaminuma et al., Eur J Immunol. (2001) 31:2669), consistent with the proposition that expansion and survival signals are required to generate a large pathogenic population. The kinetic blocking data described herein revealing maximal inhibition when OX40/OX40L interactions are absent at the time of initial antigen challenge support this, along with the idea that OX40 signals are required early (0-48 hr) and most likely provided in the secondary lymphoid organs. Further consistent with the role of OX40 signaling regulating subsequent generation or survival of memory effector T cells after antigen re-activation, primed OX40-deficient Th2 cells were capable of proliferating initially in the recall response, but did not subsequently accumulate in high numbers.

The data described herein is contrary to previous studies that memory T cells largely had a reduced requirement for costimulatory signals; rather than becoming costimulation independent, T cells may, after antigen exposure, become more reliant on other molecules such as OX40. Recent studies on an inducible Ig family member, ICOS, support this hypothesis (Gonzalo et al., Nat Immunol. (2001) 2:597). These latter data in another asthma model showed that blocking B7RP-1-ICOS interactions effectively inhibited asthmatic symptoms at the time of allergen exposure, producing similar results as OX40 described herein. Unlike OX40, ICOS had been proposed to primarily regulate cytokine production rather than T cell survival (Coyle et al., Immunity (2000) 13:95). Thus, both OX40 and ICOS may act in concert but dictate distinct phases during the Th2 recall response.

In conclusion, OX40/OX40L interactions have a critical role in the recall response, for the subsequent activation and recruitment of memory effector CD4 T cells into the airway, and for the induction of morphological changes to the airways analagous to human asthma. Since CD4$^+$ T cells have been shown to play a critical role in both initiation and maintenance of allergic pulmonary responses these results indicate that a viable therapeutic strategy is to inhibit OX40/OX40L interactions in order to reduce one or more of the symptoms. For example, molecules that inhibit expression, activity or OX40/OX40L signaling, such as anti-OX40L antibodies, alone or in combination with other therapies. This approach has a distinct advantage over blocking production of several Th2 cytokines simultaneously rather than suppressing activity, expression or signaling of a single cytokine.

What is claimed is:

1. A method of reducing or inhibiting a recall immune response in a subject having a recall response in spleen, lymph node or lymphatic vessel, or skin, comprising administering to the subject an amount of an antibody that binds to OX40 and that reduces or inhibits OX40 or OX40L signaling, expression or activity sufficient to reduce or inhibit the recall immune response in spleen, lymph node or lymphatic vessel, or skin.

2. The method of claim 1, wherein said immune response is mediated at least in part by OX40 or OX40 ligand (OX40L).

3. The method of claim 1, wherein the recall response is a secondary, tertiary or subsequent immune response to an antigen.

4. The method of claim 1, wherein the subject is mammalian.

5. The method of claim 4, wherein the mammalian subject is a human.

6. A method of alleviating or ameliorating a symptom that affects or is in spleen, lymph nodes or lymphatic vessels, or skin, associated with a secondary or subsequent immune response to an antigen in a subject having a symptom that affects or is in spleen, lymph nodes or lymphatic vessels, or skin, associated with a secondary or subsequent immune response to an antigen, comprising administering an amount of an antibody that binds to OX40 and that reduces or inhibits OX40 or OX40L signaling, expression or activity to the subject sufficient to alleviate or ameliorate the symptom that affects or is in spleen, lymph nodes or lymphatic vessels, or skin.

7. A method of alleviating or ameliorating a symptom that affects or is in spleen, lymph nodes or lymphatic vessels, or skin, associated with a secondary or subsequent immune response to an antigen in a subject having a symptom that affects or is in spleen, lymph nodes or lymphatic vessels, or skin, associated with a secondary or subsequent immune response to an antigen, wherein said response is mediated at least in part by OX40 signaling, comprising administering an amount of an antibody that binds to OX40 and that reduces or inhibits OX40 or OX40L signaling, expression or activity to the subject sufficient to alleviate or ameliorate the symptom that affects or is in spleen, lymph nodes or lymphatic vessels, or skin.

8. The method of claim 6 or 7, wherein the immune response comprises an OX40 mediated T cell response.

9. The method of claim 8, wherein the OX40 mediated T cell response contributes to inflammation.

10. A method of reducing or inhibiting one or more symptoms associated with a secondary or subsequent immune response to an antigen that affects or is in skin, spleen, lymph nodes or lymphatic vessels, comprising administering an amount of an antibody that binds to OX40 sufficient to reduce or inhibit OX40 or OX40L signaling, expression or activity, to a subject having one or more symptoms associated with a secondary or subsequent immune response that affects or is in skin, spleen, lymph nodes or lymphatic vessels thereby reducing or inhibiting one or more symptoms associated with a secondary or subsequent immune response that affects or is in skin, spleen, lymph nodes or lymphatic vessels.

11. A method of reducing or inhibiting one or more symptoms associated with a secondary or subsequent immune response to an antigen, wherein said response is mediated at least in part by OX40 mediated T cell response, and wherein said response affects or is in skin, spleen, lymph nodes or lymphatic vessels, comprising administering to a subject having one or more symptoms associated with a secondary or subsequent immune response mediated at least in part by OX40 mediated T cell response that affects or is in skin, spleen, lymph nodes or lymphatic vessels an amount of an antibody that binds to OX40 sufficient to reduce or inhibit OX40 mediated T cell response, thereby reducing or inhibiting one or more symptoms associated with a secondary or subsequent immune response that affects or is in skin, spleen, lymph nodes or lymphatic vessels.

12. The method of claim 6, 7, 10 or 11, wherein the antibody that binds to OX40 is administered to a mammalian subject.

13. The method of claim 12, wherein the mammalian subject is a human.

14. A method of decreasing inflammation associated with a memory response, wherein the inflammation affects or is in skin, spleen, lymph nodes or lymphatic vessels, comprising administering to a subject having inflammation associated with a memory response that affects or is in skin, spleen, lymph nodes or lymphatic vessels an amount of an antibody that binds to OX40 sufficient to reduce or inhibit OX40 or OX40L signaling, expression or activity, thereby decreasing the inflammation associated with a memory response.

15. The method of claim 14, wherein the inflammation is prevented or eliminated.

16. A method of decreasing a T cell inflammatory memory response, wherein the T cell inflammatory memory response affects or is in skin, spleen, lymph nodes or lymphatic vessels, comprising administering to a subject having inflammation associated with a T cell inflammatory memory response that affects or is in skin, spleen, lymph nodes or lymphatic vessels an amount of an antibody that binds to OX40 sufficient to reduce or inhibit OX40 or OX40L signaling, expression or activity, thereby decreasing the T cell inflammatory memory response that affects or is in skin, spleen, lymph nodes or lymphatic vessels.

17. The method of claim 16, wherein the T cell inflammatory memory response is prevented or eliminated.

18. The method of claim 14 or 16, wherein the antibody that binds to OX40 is administered to a mammalian subject.

19. The method of claim 18, wherein the mammalian subject is a human.

20. The method of claims 1, 6, 7, 10, 11, 14, or 16, wherein the antibody is mammalian.

21. The method of claims 1, 6, 7, 10, 11, 14, or 16, wherein the antibody is human.

22. The method of claims 1, 6, 7, 10, 11, 14, or 16, wherein the antibody is humanized.

23. The method of claims 1, 6, 7, 10, 11, 14, or 16, wherein the subject has a symptom of dermatitis.

24. The method of claims 1, 6, 7, 10, 11, 14, or 16, wherein the subject has a symptom of eczema.

* * * * *